US008633177B2

(12) United States Patent
Miranda et al.

(10) Patent No.: US 8,633,177 B2
(45) Date of Patent: Jan. 21, 2014

(54) NITROXYL (HNO) RELEASING COMPOUNDS AND USES THEREOF IN TREATING DISEASES

(75) Inventors: Katrina M. Miranda, Tucson, AZ (US); David A. Wink, Hagerstown, MD (US); Debra J. Salmon, Tucson, AZ (US); Debashree Basudhar, Tucson, AZ (US); Larry K. Keefer, Bethesda, MD (US); Joseph E. Saavedra, Thurmont, MD (US); Daniela Andrei, Elmwood Park, IL (US)

(73) Assignees: The United States of America, as represented by the Secretary, Department of Health and Human Services, Bethesda, MD (US); The Arizona Board of Regents, on behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 13/582,487

(22) PCT Filed: Mar. 18, 2011

(86) PCT No.: PCT/US2011/029072
§ 371 (c)(1),
(2), (4) Date: Nov. 30, 2012

(87) PCT Pub. No.: WO2011/116336
PCT Pub. Date: Sep. 22, 2011

(65) Prior Publication Data
US 2013/0065863 A1 Mar. 14, 2013

Related U.S. Application Data

(60) Provisional application No. 61/349,716, filed on May 28, 2010, provisional application No. 61/315,604, filed on Mar. 19, 2010.

(51) Int. Cl.
*A61K 31/655* (2006.01)
*C07C 245/24* (2006.01)
(52) U.S. Cl.
USPC .......................................... 514/150; 534/552
(58) Field of Classification Search
None
See application file for complete search history.

(56) References Cited

U.S. PATENT DOCUMENTS

| 4,863,457 | A | 9/1989 | Lee |
| 4,954,526 | A | 9/1990 | Keefer |
| 5,378,475 | A | 1/1995 | Smith et al. |
| 5,443,505 | A | 8/1995 | Wong et al. |
| 6,379,660 | B1 | 4/2002 | Saavedra et al. |
| 6,511,991 | B2 | 1/2003 | Hrabie et al. |
| 6,936,639 | B2 | 8/2005 | Wink et al. |
| 2004/0038947 | A1 | 2/2004 | Wink et al. |
| 2004/0039063 | A1 | 2/2004 | Wink et al. |
| 2005/0009789 | A1 | 1/2005 | Wink et al. |
| 2005/0192254 | A1 | 9/2005 | Wink et al. |
| 2009/0246296 | A1 | 10/2009 | Wink et al. |

FOREIGN PATENT DOCUMENTS

| WO | WO 2006/125016 A1 | 11/2006 |
| WO | WO 2007/044963 A2 | 4/2007 |
| WO | WO 2007/127725 A2 | 11/2007 |
| WO | WO 2011/116336 A1 | 9/2011 |

OTHER PUBLICATIONS

Abdellatif et al. Bioorg. Med. Chem. 16 (2008) 6528-6534.*
Antonini et al., "The derivatives of ferrous hemoglobin and myoglobin," *Frontiers Biol.*, Ch. 2, 13-39 (1971).
Birchmeier et al., "Cadherin expression in carcinomas: role in the formation of cell junctions and the prevention of invasiveness," *Biochim. Biophys. Acta.*, 1198 (1), 11-26 (1994).
Davies et al., "Aspirin causes rapid up-regulation of cyclo-oxygenase-2 expression in the stomach of rats," *Aliment. Pharmacol. Ther.*, 11 (6), 1101-1108 (1997).
Drago et al., "The Reaction of Nitrogen(II) Oxide with Various Primary and Secondary Amines," *J. Am. Chem. Soc.*, 83 (8), 1819-1822 (1961).
Espey et al., "Ingress and reactive chemistry of nitroxyl-derived species within human cells," *Free Radic. Biol. Med.*, 33 (6), 827-834 (2002).
Feelisch et al., "Donors of Nitrogen Oxides," *Methods in Nitric Oxide Research*, Ch. 7, 71-115 (1996).
Forrester et al. "Nitric oxide-induced p53 accumulation and regulation of inducible nitric oxide synthase expression by wild-type p53," *Proc. Natl. Acad. Sci. USA*, 93 (6), 2442-2447 (1996).
Gatenby et al., "Why do cancers have high aerobic glycolysis?," *Nat. Rev. Cancer*, 4 (11), 891-899 (2004).
Guillory, "Generation of Polymorphs, Hydrates, Solvates, and Amorphous Solids," *Drugs and the Pharmaceutical Sciences*, 95, 183-226 (1999).
Horstmann et al., "Release of nitric oxide from novel diazeniumdiolates monitored by laser magnetic resonance spectroscopy," *Nitric Oxide*, 6 (2), 135-141 (2002).
Isenberg et al., "Thrombospondin-1 antagonizes nitric oxide-stimulated vascular smooth muscle cell responses," *Cardiovasc. Res.*, 71 (4), 785-793 (2006).

(Continued)

*Primary Examiner* — Jason M Nolan
*Assistant Examiner* — Ana Z Muresan
(74) *Attorney, Agent, or Firm* — Leydig, Voit & Mayer

(57) ABSTRACT

Disclosed is a compound of the formula (I) or a pharmaceutically acceptable salt thereof: (I) in which $R^1$, $R^2$, $R^3$, and $R^4$ are defined herein and pharmaceutical compositions thereof. Further provided is a method of treating various disorders, such as a disorder selected from the group consisting of a cardiovascular disorder, cancer, chronic pain, alcohol dependence, and inflammation in a patient comprising administering an effective amount of a compound or pharmaceutically acceptable salt of formula (I).

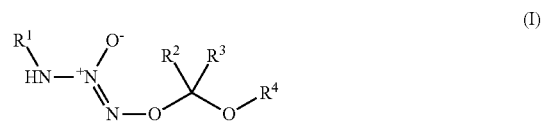

34 Claims, 10 Drawing Sheets

(56) References Cited

OTHER PUBLICATIONS

International Preliminary Report on Patentability, Application No. PCT/US2011/029072, dated Oct. 4, 2012.

International Search Report, Application No. PCT/US2011/029072, dated Jun. 15, 2011.

Issaeva et al., "Rescue of mutants of the tumor suppressor p53 in cancer cells by a designed peptide," *Proc. Natl. Acad. Sci. USA*, 100 (23), 13303-13307 (2003).

Karbowski et al. "Dynamics of mitochondrial morphology in healthy cells and during apoptosis," *Cell Death Differ.*, 10 (8), 870-880 (2003).

Keefer et al., "NONOates" (1-substituted Diazen-1-ium-1,2-diolates) as nitric oxide donors: convenient nitric oxide dosage forms, *Methods Enzymol.*, 268, 281-293 (1996).

Kitamura et al., "In vivo nitric oxide measurements using a microcoaxial electrode," *Methods Mol. Biol.*, 279, 35-43 (2004).

Kojima et al., "Development of a fluorescent indicator for nitric oxide based on the fluorescein chromophore," *Chem. Pharm. Bull.*, 46 (2), 373-375 (1998).

Lopez et al., "Inhibition of yeast glycolysis by nitroxyl (HNO): A mechanism of HNO toxicity and implications to HNO biology," *Arch. Biochem. Biophys.*, 442 (1), 140-148 (2005).

Maragos et al., "Complexes of NO with nucleophiles as agents for the controlled biological release of nitric oxide. Vasorelaxant effects," *J. Med. Chem.*, 34 (11), 3242-3247 (1991).

Miranda et al., "Donors of HNO," *Curr. Top. Med. Chem.*, 5 (7), 649-664 (2005).

Miranda et al., "Comparison of the NO and HNO donating properties of diazeniumdiolates: primary amine adducts release HNO in Vivo," *J. Med. Chem.*, 48 (26), 8220-8228 (2005).

Nath et al., "Nitro-aspirin inhibits MCF-7 breast cancer cell growth: effects on COX-2 expression and Wnt/β-catenin/TCF-4 signaling," *Biochem. Pharmacol.*, 78 (10), 1298-1304 (2009).

Nguyen et al., "Hantzsch 1,4-dihydropyridines containing a diazen-1-ium-1,2-diolate nitric oxide donor moiety to study calcium channel antagonist structure-activity relationships and nitric oxide release," *Bioorg. Med. Chem.*, 13 (5), 1725-1738 (2005).

Norris et al., "Nitroxyl inhibits breast tumor growth and angiogenesis," *Int. J. Cancer*, 122 (8), 1905-1910 (2008).

O'Connell et al., "Isolation and Culture of Adult Mouse Cardiac Myocytes for Signaling Studies," *AfCS Research Reports*, 1 (5), 1-9 (2003).

Reichenbach et al., "Reaction mechanism between nitric oxide and glutathione mediated by Fe(III) myoglobin," *Nitric Oxide*, 5 (4), 395-401 (2001).

Ridnour et al., "The biphasic nature of nitric oxide responses in tumor biology," *Antioxid. Redox Signaling*, 8 (7 & 8), 1329-1337 (2006).

Saavedra et al., "Esterase-Sensitive Nitric Oxide Donors of the Dlazeniumdiolate Family: In Vitro Antileukemic Activity," *J. Med. Chem.*, 43 (2), 261-269 (2000).

Salmon et al., "HNO-releasing diazeniumdiolates as alcohol deterrent agents," *ACS Abstract* (2010).

Shafirovich et al., "Nitroxyl and its anion in aqueous solutions: spin states, protic equilibria, and reactivities toward oxygen and nitric oxide," *PNAS*, 99 (11), 7340-7345 (2002).

Velázquez et al., "Novel nonsteroidal antiinflammatory drugs possessing a nitric oxide donor diazen-1-ium-1,2-diolate moiety: design, synthesis, biological evaluation, and nitric oxide release studies," *J. Med. Chem.*, 48, 4061-4067 (2005).

Written Opinion of the International Searching Authority, Application No. PCT/US2011/029072, dated Jun. 15, 2011.

\* cited by examiner

NITROXYL (HNO) RELEASING COMPOUNDS AND USES THEREOF IN TREATING DISEASES

CROSS-REFERENCE TO RELATED APPLICATIONS

This patent application is the U.S. national phase of International Application No. PCT/US2011/029072, filed on Mar. 18, 2011, which claims the benefit of U.S. Provisional Patent Application No. 61/315,604, filed Mar. 19, 2010 and U.S. Provisional Patent Application No. 61/349,716, filed May 28, 2010, each of which is incorporated by reference in its entirety herein.

BACKGROUND OF THE INVENTION

Nitroxyl (HNO) is an elusive chemical species that has been shown to possess intriguing biological properties. For example, nitroxyl has been implicated in the mechanism of cyanamide's inhibitory effect on aldehyde dehydrogenase in treating alcohol abuse as well as reversing experimental heart failure.

Despite HNO having been described in the chemical literature for decades, there are surprising gaps in the literature that complicate the rational exploitation of its pharmacological properties. Historically, Angeli's salt (AS) has been known to generate HNO in solution. Recently, IPA/NO (1, the sodium salt of diazeniumdiolated isopropylamine) has been shown to mimic AS in its chemical and biological properties. Unfortunately, neither of these salts are suitable from the drug development perspective since both are difficult to purify.

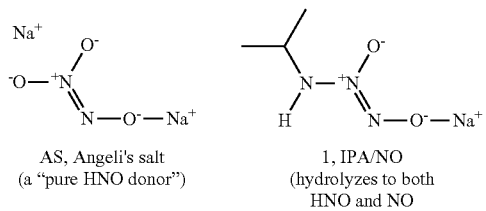

AS, Angeli's salt
(a "pure HNO donor")

1, IPA/NO
(hydrolyzes to both HNO and NO)

Thus, there remains an unmet need for compounds that can generate reliable, controlled fluxes of HNO in physiological media or conditions. In addition, there exists an unmet need for compounds that release both HNO and drugs such as non-steroidal anti-inflammatory drugs (NSAID).

BRIEF SUMMARY OF THE INVENTION

An embodiment of the invention provides a compound of the formula (I) or a pharmaceutically acceptable salt thereof:

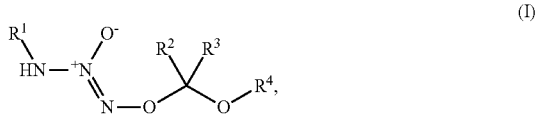

(I)

wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thio-alkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity.

A compound of formula (I) or a salt thereof undergoes a slower hydrolysis than 1 at physiological pH, such that the compound of formula (I) generates a correspondingly lower steady-state concentration of HNO, minimizing its dimerization/dehydration to $N_2O$. As a result, a compound of formula (I) or a salt thereof releases HNO that is more efficiently available to biological targets for therapeutic uses.

The compounds of formula (I), wherein $R^4$ is a non-steroidal anti-inflammatory drug (NSAID) moiety retaining its NSAID activity, combine the advantages of HNO release and the advantageous properties of NSAIDS. They provide increased efficacy against cancer and cardiovascular disease.

The invention further provides a pharmaceutical composition and a method of treating various disorders, for example, a cardiovascular disorder, cancer, chronic pain, alcohol dependence, or inflammation, in a patient comprising administering an effective amount of a compound or salt of formula (I).

In a specific advantage, the compounds of the invention are useful in chemopreventing as well as treating cancers.

BRIEF DESCRIPTION OF THE SEVERAL VIEWS OF THE DRAWINGS

In FIG. 4A, spectra were collected every 60 s (10-min intervals shown) after dissolving 2 in PBS (pH 7.4) at 37° C., and only loss of the parent compound was observed. In FIG. 4B, the pH was elevated to 12, and scans were collected every 0.5 s (through 2.5 s and 3.5, 5.5, 9.5, and 54.5 shown). In FIG. 4C, porcine liver esterase (20 μL in 3 mL) was added (pH 7.4), and spectra were collected every 10 s. Hydrolysis of 2 ($\lambda_{max}$ 236 nm) to 1 ($\lambda_{max}$ 250 nm) was complete within 40 s (0.067 s$^{-1}$) under these conditions. The rate of decay of 1 in FIG. 4C was comparable to that shown in FIG. 3A (0.0033 s$^{-1}$ vs. 0.0012 s$^{-1}$, respectively). Elevation of the intensity near 200 nm indicated formation of autoxidation products such as nitrite. Deaeration inhibited this peak (data not shown).

(FIG. 6B) with DAF-FM loaded both inside and outside cells (FIG. 6C) DAF-FM loaded inside A549 cells (n=4).

DETAILED DESCRIPTION OF THE INVENTION

Figure 1A:
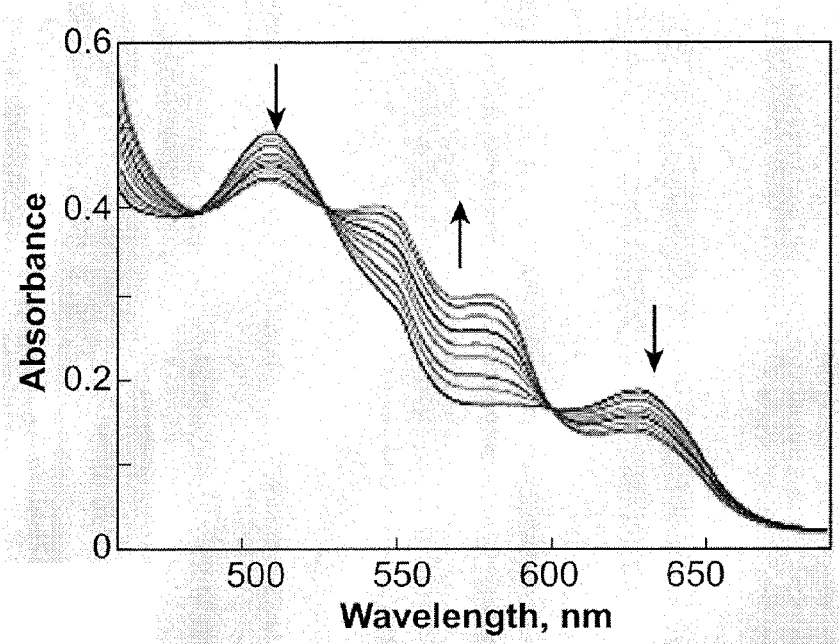
FIGS. 1A and 1B are graphs illustrating the reductive nitrosylation of metMb (50 μM) by (FIG. 1A) IPA/NO, 1 (100 μM), or (FIG. 1B) AcOM-IPA/NO, 2 ($O^2$-(acetoxymethyl) 1-(isopropylamino)diazen-1-ium-1,2-diolate; 100 μM) in an embodiment of the invention. The assay was performed in phosphate buffered saline (PBS), pH 7.4, containing 50 μM DTPA at 37° C. under deaerated conditions and was followed until there were no further spectral changes at 543 and 575 nm (1, 2, 4, 6, 9, 14, 23 and 46 min for 1; 3-107 min in 4- to 10-min intervals shown for 2).

An embodiment of the invention provides a compound of the formula (I) or a pharmaceutically acceptable salt thereof:

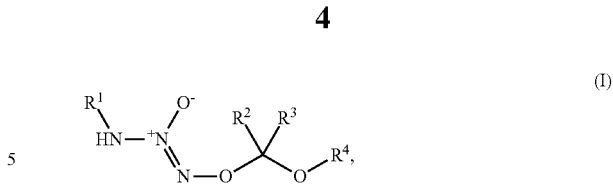

wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^4$ is —C(═O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity.

Each of $C_{1-12}$ alkyl, $C_{3-12}$ alkenyl, $C_{3-12}$ alkynyl, $C_{3-8}$ cycloalkyl, aryl, and heteroaryl can be substituted with one or more substituents (e.g., 1 to 5, 1 to 4, 1 to 3, 1 or 2) selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino. In some embodiments, one or more substituents are selected from the group consisting of halo, OH, CN, hydroxy-$C_{1-6}$ alkyl, halo-$C_{1-6}$ alkyl, amino-$C_{1-6}$ alkyl, $C_{1-6}$ alkoxy, aryloxy, $C_{1-6}$ thioalkoxy, nitro, sulfonato, $C_{1-6}$ acyl, $C_{2-6}$ acyloxy, carboxyl, mercapto, $C_{1-6}$ alkoxy-carbonyl, $C_{1-6}$ alkoxy-carbonyloxy, amido, amino, $C_{1-6}$ alkylamino, and di-$C_{1-16}$ alkyl-amino. When an aryl or heteroaryl group is substituted with a substituent described herein, a hydrogen on the aryl or heteroaryl ring is replaced with the substituent and this can take place in any of the available hydrogens, e.g., 2, 3, 4, 5, and/or 6-position, if the 1-position is the point of attachment of the aryl group in the compound of the present invention.

In certain embodiments, $R^1$ is optionally substituted $C_{1-12}$ alkyl, optionally substituted alkenyl (e.g., allyl), or optionally substituted $C_{3-8}$ cycloalkyl (e.g., cyclopentyl, cyclohexyl, bicyclo[2.2.1]heptyl) in the compound of formula (I) or a salt thereof. In a preferred embodiment, $R^1$ is optionally substituted $C_{1-12}$ alkyl or $C_{1-4}$ alkyl, e.g., isopropyl or ethyl. In combination with any of the embodiments described herein, $R^2$ and $R^3$ preferably are the same or different and each is selected from the group consisting of hydrogen, $C_{1-12}$ alkyl, aryl, or heteroaryl, each of which, other than hydrogen, is optionally substituted. In combination with any of the embodiments described herein, $R^2$ and $R^3$ are particularly hydrogen.

In certain embodiments, $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino.

In certain embodiments, $R^4$ a non-steroidal anti-inflammatory drug (NSAID) moiety retaining its NSAID activity. The NSAID moiety may be any suitable NSAID moiety. In an embodiment, the NSAID moiety is selected from the group consisting of aspirin, propionic acid derivatives, acetic acid derivatives, sulphonanilides, licofelone, enolic acid derivatives, fenamic acid derivatives, and selective COX-2 inhibitors. Specific examples of NSAID moieties include, but are not limited to the NSAID is selected from the group consisting of aspirin, ibuprofen, naproxen, fenoprofen, ketoprofen, flurbiprofen, oxaprozin, indomethacin, sulindac, etodolac, diclofenac, piroxicam, meloxicam, tenoxicam, droxicam, lomoxicam, isoxicam, mefenamic acid, meclofenamic acid, flufenamic acid, tolfenamic acid, celecoxicab, rofecoxib, valdecoxib, parecoxib, lumiracoxib, etoricoxib, nimesulide, licofenac, and niflumic acid.

In any of the above embodiments, $R^2$ and $R^3$ are hydrogen in the compound of formula (I) or a salt thereof and/or $R^1$ is optionally substituted $C_{1-12}$ alkyl and/or $R^4$ is —C(=O)$R^5$, wherein $R^5$ is an optionally substituted $C_{1-12}$ alkyl. In a preferred embodiment, the compound of formula (I) is

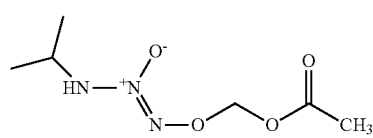

$O^2$-(acetoxymethyl)1-(isopropylamino)diazen-1-ium-1,2-diolate (AcOM-IPA/NO, 2) or a salt thereof.

In an embodiment, the compound of formula (I) or salt thereof is selected from the group consisting of formulas (101)-(115) below, wherein $R^1$, $R^2$, and $R^3$ are as defined above:

(101)

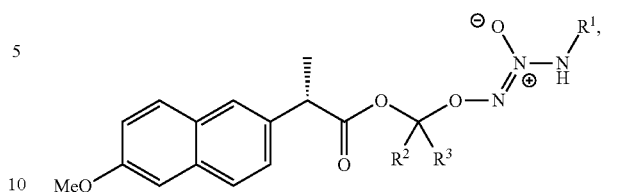

(102)

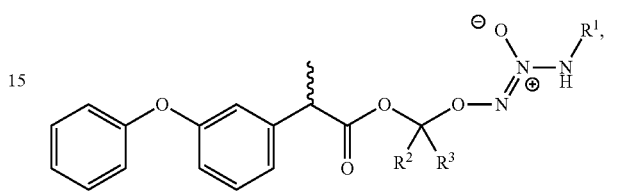

(103)

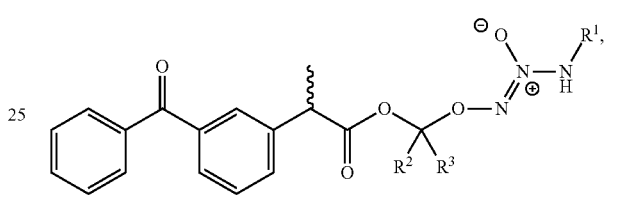

(104)

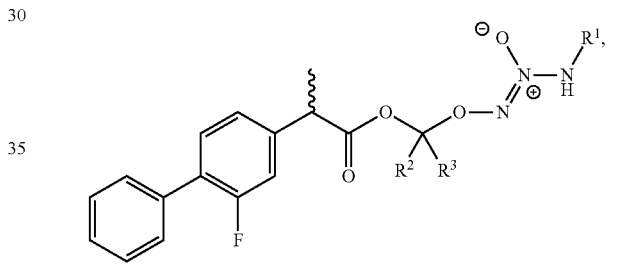

(105)

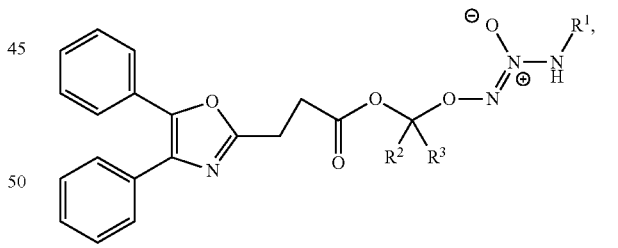

(106)

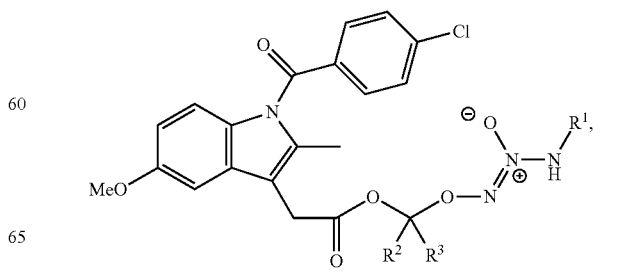

(107)

(108)
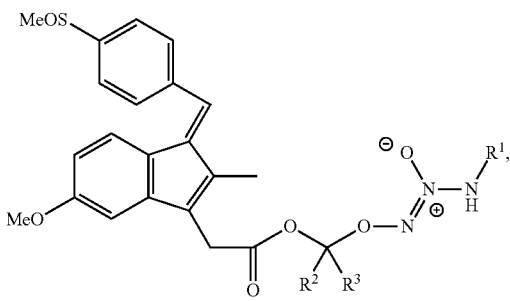

(109)
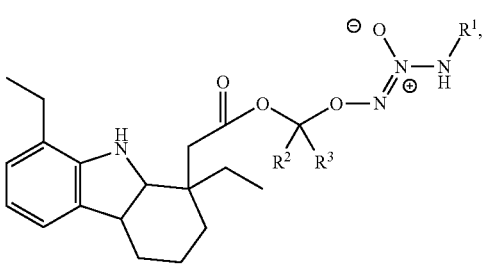

(110)
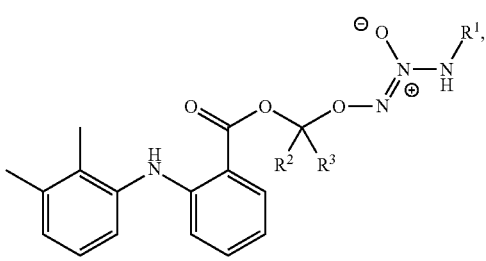

(111)
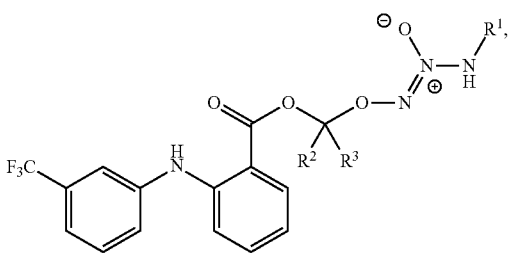

(112)
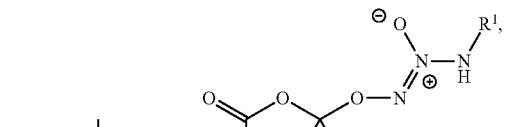

(113)
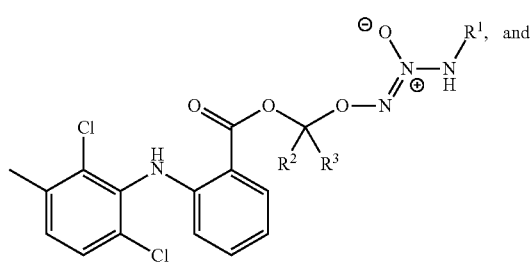

(114)
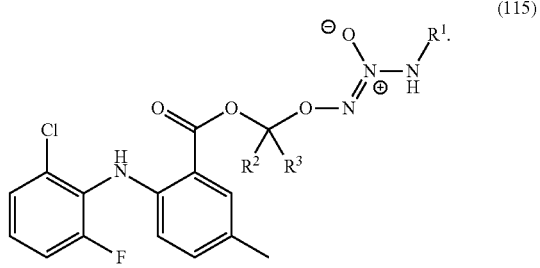

(115)
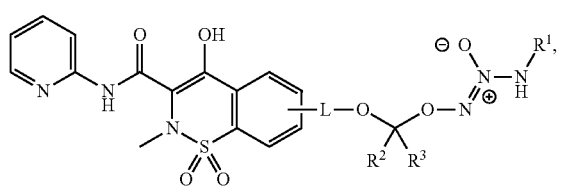

In an embodiment, the compound of formula (II) or salt thereof is selected from the group consisting of formulas (116)-(125) below, wherein $R^1$, $R^2$, and $R^3$ are as defined above, and wherein L is a linking group selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted arylalkyl, carbonyl, thiocarbonyl, iminocarbonyl, carboxyl, and carbamoyl:

(116)
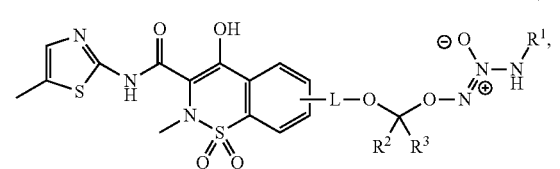

(117)

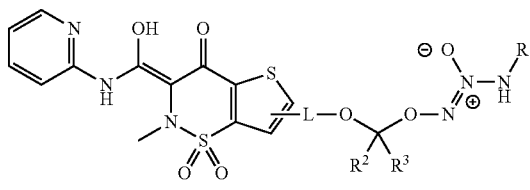
(118)

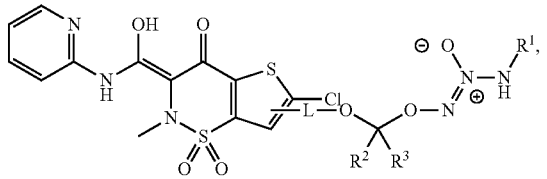
(119)

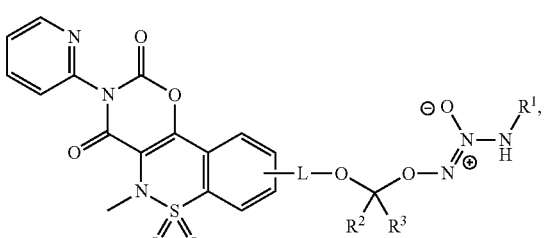
(120)

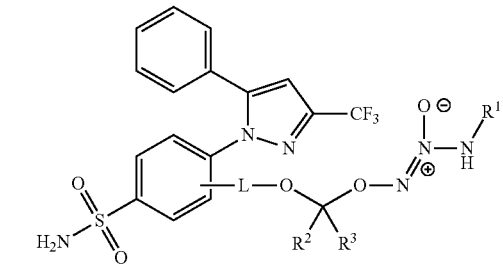
(121)

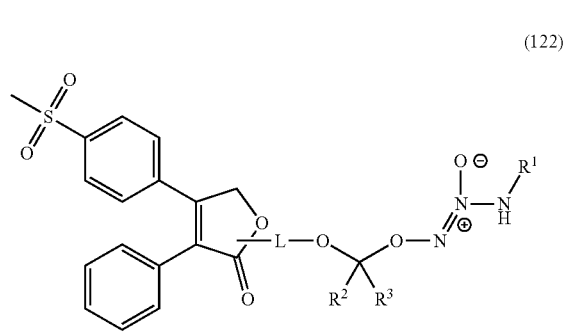
(122)

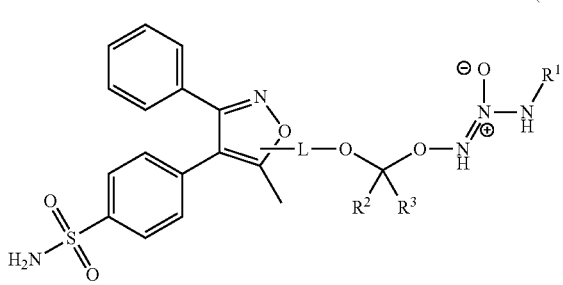
(123)

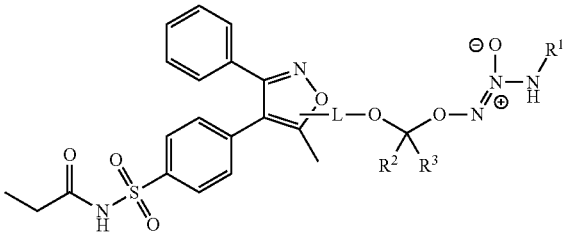
(124)

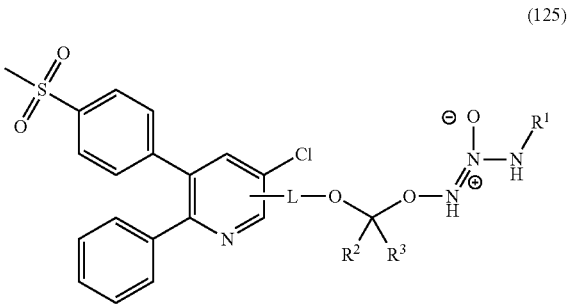
(125)

Preferably, the NSAID of $R^4$ of the compound or salt of formula (I) is selected from the group consisting of aspirin, ibuprofen, and diclofenac. An especially preferred NSAID is aspirin. In this regard, the compound or salt of formula (I) can be selected from the group consisting of formulas (126)-(128) below, wherein $R^1$, $R^2$, and $R^3$ are as defined above:

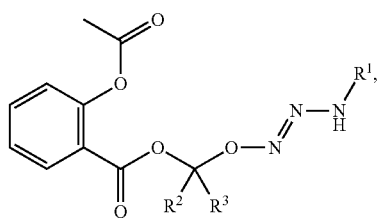
(126)

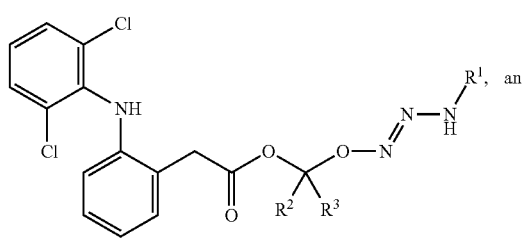
(127)

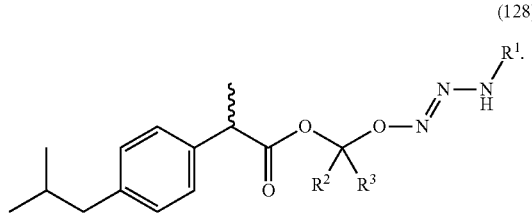
(128)

In any of the embodiments above, the term "alkyl" implies a straight-chain or branched alkyl substituent containing from, for example, about 1 to about 12 carbon atoms, preferably from about 1 to about 8 carbon atoms, more preferably from about 1 to about 6 carbon atoms. In accordance with an embodiment, the alkyl group is preferably a $C_1$-$C_3$ alkyl.

Examples of alkyl group include methyl, ethyl, n-propyl, isopropyl, n-butyl, sec-butyl, isobutyl, tert-butyl, n-pentyl, isopentyl, n-hexyl, and the like. This definition also applies wherever "alkyl" occurs, such as in hydroxyalkyl, monohalo alkyl, dihalo alkyl, and trihalo alkyl.

In any of the embodiments above, the term "alkenyl," as used herein, means a linear or branched alkenyl substituent containing from, for example, about 2 to about 12 or about 3 to about 12 carbon atoms, preferably from about 3 to about 8 carbon atoms, more preferably from about 3 to about 6 carbon atoms. In accordance with an embodiment, the alkenyl group is preferably a $C_3$-$C_6$ alkenyl. Examples of alkenyl group include allyl, 1-butenyl, 2-butenyl, 1-pentenyl, 2-pentenyl, 3-pentenyl, 1-hexenyl, and the like. A preferred alkenyl is allyl.

In any of the embodiments above, the term "alkynyl," as used herein, means an alkynyl substituent, linear or branched, containing at least one carbon-carbon triple bond and linear alkynyls contain from, for example, about 3 to about 12 carbon atoms (branched alkynyls are about 4 to about 12 carbons atoms), preferably from about 3 to about 8 carbon atoms (branched alkynyls are preferably from about 4 to about 8 carbon atoms), more preferably from about 3 to about 6 carbon atoms. Examples of such substituents include propynyl, propargyl, n-butynyl, pentynyl, isopentynyl, hexynyl, octynyl, dodecynyl, and the like.

In any of the embodiments above, the term "cycloalkyl," as used herein, means a cyclic alkyl substituent containing from, for example, about 3 to about 8 carbon atoms, preferably from about 5 to about 8 carbon atoms, more preferably from about 5 to about 6 carbon atoms. Examples of such substituents include cyclopropyl, cyclobutyl, cyclopentyl, cyclohexyl, bicyclo[2.2.1]heptyl (e.g., (1s,4s)-bicyclo[2.2.1]heptyl), and the like.

In any of the embodiments above, the term "heterocyclyl" means a stable, saturated, or partially unsaturated monocyclic, bicyclic, and spiro ring system containing 3 to 7 ring members of carbon atoms and other atoms selected from nitrogen, sulfur, and/or oxygen. Preferably, a heterocyclyl is a 5, 6, or 7-membered monocyclic ring and contains one, two, or three heteroatoms selected from nitrogen, oxygen, and/or sulfur. The heterocyclyl may be attached to the parent structure through a carbon atom or through any heteroatom of the heterocyclyl that results in a stable structure. Examples of heterocyclic rings are thiazolinyl, imidazolidinyl, piperazinyl, homopiperazinyl, pyrrolyl, pyrrolinyl, pyrazolyl, pyranyl, piperidyl, and morpholinyl.

In any of the embodiments above, the term "aryl" refers to an unsubstituted or substituted aromatic carbocyclic moiety, as commonly understood in the art, and includes monocyclic, bicyclic, and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise $4n+2\pi$ electrons, according to Hückel's Rule, wherein n=1, 2, or 3.

In any of the embodiments above, the term "heteroaryl" refers to aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized, and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. Illustrative examples of heteroaryl groups are pyridinyl, pyridazinyl, pyrimidyl, pyrazinyl, benzimidazolyl, triazinyl, imidazolyl, (1,2,3)- and (1,2,4)-triazolyl, pyrazinyl, tetrazolyl, furyl, thienyl, isothiazolyl, thiazolyl, oxazolyl, isoxazolyl, and oxadiazolyl.

In any of the embodiments above, the term "alkoxy" embraces linear or branched alkyl groups that are attached to divalent oxygen. The alkyl group is the same as described herein. Examples of alkoxy group include methoxy, ethoxy, n-propoxy, isopropoxy, n-butoxy, sec-butoxy, isobutoxy, tert-butoxy, n-pentoxy, isopentoxy, n-hexoxy, and the like. In accordance with an embodiment, the alkoxy group is preferably a $C_1$-$C_3$ alkoxy. The term "thioalkoxy" refers to substituents in which linear or branched alkyl groups are attached to divalent sulfur. The alkyl group is the same as described herein. The term "aryloxy" refers to substituents that have an aryl group attached to divalent oxygen. The aryl group is the same as described herein. Examples of such substituents include phenoxy.

In any of the embodiments above, the term "halo" refers to a halogen selected from the group consisting of fluorine, chlorine, bromine, and iodine, preferably chlorine or bromine.

In any of the embodiments above, the term "amino" refers to —$NH_2$. The term "$C_{1-12}$ alkylamino" refers to a secondary amine substituent with one hydrogen and one $C_{1-12}$ alkyl group directly attached to a trivalent nitrogen atom. The term "di-$C_{1-12}$ alkyl-amino" refers to a tertiary amine substituent with two of the same or different $C_{1-12}$ alkyl groups directly attached to a trivalent nitrogen atom. The $C_{1-12}$ alkyl group is the same as described herein.

In any of the embodiments above, the term "carboxy" refers to the group —C(O)OH. The term "$C_{1-12}$ alkoxy-carbonyl" refers to the group —OC(O)R, in which R is a $C_{1-12}$ alkyl group as described herein.

In any of the embodiments above, the terms "$C_1$ acyl" and "$C_{2-12}$ acyl" refer to the groups —C(O)—H and —C(O)—$C_{1-12}$ alkyl, respectively. The term "$C_{2-12}$ acyloxy" refers to the group —OC(O)—$C_{1-12}$ alkyl. R is a $C_{1-12}$ alkyl group as described herein.

In any of the embodiments above, the term "amido" refers to the group —C(O)$NH_2$.

In any of the embodiments above, the terms "hydroxyalkyl," "haloalkyl," and "aminoalkyl" refer to an alkyl group, as described herein, that has a hydroxyl, halo, or amino substituent, respectively. The substituent can be on any suitable carbon of the alkyl group (e.g., at the 1-, 2-, 3-, 4-, 5-, 6-, 7-, 8-, 9-, 10-, 11-, or 12-position).

In any of the embodiments above, whenever a range of the number of atoms in a structure is indicated (e.g., a $C_{1-12}$, $C_{1-8}$, $C_{1-6}$, or $C_{1-4}$ etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any subrange thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In any of the embodiments above, the phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media such as ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445, and *Journal of Pharmaceutical Science*, 66, 2-19 (1977). For example, they can be a salt of an alkali metal (e.g., sodium or potassium), alkaline earth metal (e.g., calcium), or ammonium of salt.

The compounds of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The invention also includes solvent addition forms ("solvates") of the compounds of the invention. Some compounds have a tendency to trap a fixed molar ratio of solvent molecules in the crystalline solid state, thus forming a solvate. When the compound of formula (I) is placed in a system in which a certain solvent is brought to a vapor form, in some situations, the compound, together with the molecules of the solvent, forms a crystal. The material formed by crystallization of the compound of formula (I) and the solvent in a three-dimensional order is called a solvate herein. The solvent can be associated with a crystalline solid form of a compound of formula (I) in various ways. The interaction can be due to weak binding (e.g., hydrogen bonding, van der Waals, and dipole-dipole) or by entrapment (e.g., liquid inclusion).

A solvate can be formed by a variety of methods, many of which are known in the art. A compound of formula (I) can be combined with one or more solvents by any suitable method (e.g., crystallization, lyophilization, film coating, spray drying, suspension, wetting, grinding, vapor sorption, etc.). For example, a compound of formula (I) can be combined with a particular solvent(s) and heated to boiling. The solution can then be slowly cooled to allow formation of the solvate crystals. Cooling can occur at room temperature or at a reduced temperature (e.g., an ice bath and/or refrigerated conditions). Controlling the temperature can be influential in the formation of solvates. Typically a lower temperature favors solvate formation. The formed solvate can be characterized by analytical methods such as thermogravimetric analysis (TGA), differential scanning calorimetry (DSC) alone or with infrared (IR) and/or mass spectrometry, x-ray powder diffraction, moisture sorption experiments, hot-stage polarized light microscopy, or a combination of these methods. Various techniques to prepare solvates are known in the art. See, e.g., J. Keith Guillory, "Generation of Polymorphs, Hydrates, and Solvates, and Amorphous Solids," *Drugs and the Pharmaceutical Sciences*, 95 (Polymorphism in Pharmaceutical Solids): 183-226 (1999); and Greisser, U., "The Importance of Solvates" in *Polymorphism*, Hilfiker, R., Ed., (Wiley-VCH Verlag GmbH & Co. KGaA: Weinheim, Germany, 2006), pages 211-233.

A solvate means a solvent addition form that contains either stoichiometric or non-stoichiometric amounts of solvent. A stoichiometric solvate implies a fixed, although not necessarily integral, ratio of solvent to compound (e.g., a solvent coordination number of 1, 2, 3, 4, 5, 6, etc.). A preferred solvent coordination number of a stoichiometric solvate is 1. A non-stoichiometric solvate can be an interstitial solid solution or an interstitial co-crystal. The solvent content of a solvate can be any suitable value, including a multiple of the molar compound ratio such that the solvent coordination number is a non-integral number (e.g., 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, etc.). The amount of solvent in the structure generally depends on the partial pressure of the solvent in the environment of the solid and the temperature (Greisser, U., "The Importance of Solvates" in *Polymorphism*, Hilfiker, R., Ed., (Wiley-VCH Verlag GmbH & Co. KGaA: Weinheim, Germany, 2006), pages 211-233).

The solvent can be any suitable solvent, i.e., the solvent is not particularly limited as long as a solvate of the compound of formula (I) can be formed. Solvents usable for solvate formation include water, alcohols, ethers, esters, alkanes, dichloromethane, chloroform, acetone, acetonitrile, toluene, tetrahydrofuran, dimethylformamide (DMF), dimethyl sulfoxide (DMSO), dioxane, and combinations thereof. In some embodiments, the solvate contains a mixture of solvents, such as a combination of two or more of the aforementioned solvents. Preferably the solvent should have relatively low toxicity and can be removed from the compound of formula (I) to a level that is acceptable according to The International Committee on Harmonization (ICH) guidelines ("ICH Q3C Impurities: Guideline for Residual Solvents, International Conference on Harmonization of Technical Requirements for Registration of Pharmaceuticals for Human Use," Geneva, Switzerland, July 1997). Preferred solvents include water, alcohols, ethers, esters, and alkanes. If the solvent is water, the solvate formed is a "hydrate," whereas when the solvent is alcohol, the solvate formed is an "alcoholate." Specific examples of preferred solvents usable for solvate formation include water, $C_{1-4}$ alcohol (e.g., methanol, ethanol, propanol, isopropanol, and n-butanol), $C_{1-4}$ ether (e.g., diethyl ether), an ester of a $C_{1-6}$ (preferably $C_{1-4}$) alkyl acetate (e.g., methyl acetate, ethyl acetate, propyl acetate, and butyl acetate), a $C_{5-7}$ alkane (e.g., pentane, hexane, and heptane), and combinations thereof. Mixed solvates include, for example, water/ethanol, water/methanol, water/acetone, water/hexane, and water/DMF.

Nitric oxide release from the diazeniumdiolated compounds described herein can be determined/detected using known techniques such as those described in U.S. Pat. Nos. 6,511,991 and 6,379,660; Keefer, et al., "NONOates(1-Substituted Diazen-1-ium-1,2 diolates) as Nitric Oxide Donors: Convenient Nitric Oxide Dosage Forms," *Methods in Enzymology*, 28: 281-293 (1996); Horstmann et al., "Release of nitric oxide from novel diazeniumdiolates monitored by laser magnetic resonance spectroscopy," *Nitric Oxide*, 6(2): 135-41 (2002); and Kitamura et al., "In vivo nitric oxide measurements using a microcoaxial electrode," *Methods Mol. Biol.*, 279: 35-44 (2004), which are incorporated herein by reference. In general, the amount of NO produced can be detected by a chemiluminescence method, electrochemical method, and/or an absorbance method. In addition, nitric oxide assay kits are commercially available.

Angeli's salt and IPA/NO (1) hydrolyze by the following mechanisms. An embodiment of the compound of formula (I) wherein $R^4$ is —C(=O)$R^5$, for example, AcOM-IPA/NO, 2, undergoes hydrolysis to the deprotected form of the compound of formula (I) i.e., $R^1NH$—$N_2O_2^-$ (and formaldehyde and acetate), in the presence of esterase. It was surprisingly discovered, however, that the deprotected form is not detected as an intermediate in the absence of esterase (i.e., uncatalyzed hydrolysis). This unexpected phenomenon is even more evident at an elevated pH. In a specific example of IPA/NO (1) and AcOM-IPA/NO (2), 1 hydrolyzes 100-fold more slowly than 2 at pH 11, but nuclear magnetic resonance (NMR) signals for 1 could not be seen during the rapid hydrolysis of 2 at this pH. By hydrolyzing an order of magnitude slower at physiological pH than 1, 2 generates a correspondingly lower steady-state concentration of HNO, minimizing its dimerization/dehydration to $N_2O$ and making the HNO much more efficiently available to biological targets (e.g., metmyoglobin and glutathione). Thus, this embodiment of the compound of formula (I) generates reliable, controlled fluxes of HNO, such that the compound of formula (I) is a prodrug of HNO for therapeutic uses. Nitroxyl (HNO) release from the compound of formula (I) or a salt thereof can be determined/detected using known techniques and/or by the methods described herein.

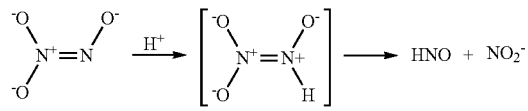

Angeli's anion

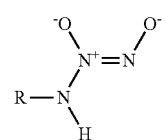

IPA/NO anion

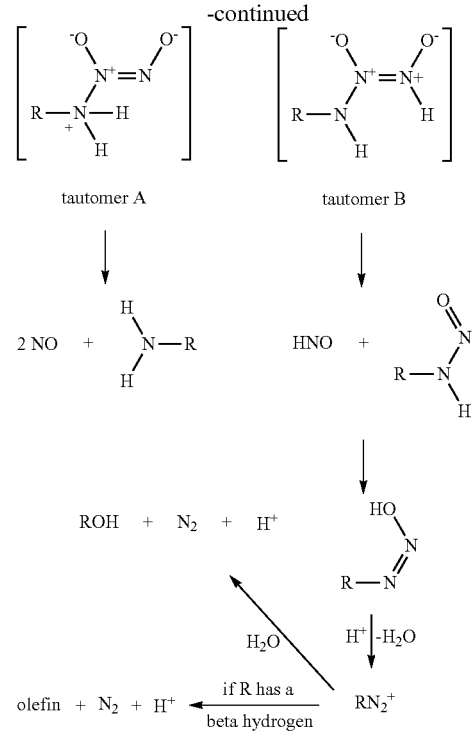

A compound of formula (I) where $R^4$ is —C(=O)$R^5$, or a salt thereof, can be prepared by the following method. An unprotected diazeniumdiolate can be prepared first (i.e., $R^1NH$—$N_2O_2^-$) by reacting a primary amine of the formula $NH_2R^1$, in which $R^1$ is described herein, with nitric oxide gas. The unprotected diazeniumdiolate can then subsequently be protected with the desired substituted methyl carboxylate (e.g., LG-CR$_2$R$_3$OC(O)(C$_{1-12}$ alkyl), LG-CR$_2$R$_3$OC(O)(C$_{2-12}$ alkenyl), LG-CR$_2$R$_3$OC(O)(C$_{2-12}$ alkynyl), LG-R$_2$R$_3$OC(O)(C$_{3-8}$ cycloalkyl), LG-R$_2$R$_3$OC(O)(heterocyclyl), LG-R$_2$R$_3$OC(O)(aryl), LG-R$_2$R$_3$OC(O)(heteroaryl), in which LG is a leaving group (e.g., Br, Cl, etc.)).

Embodiments of the compounds of formula (I) or a salt thereof where $R^4$ is a non-steroidal anti-inflammatory drug (NSAID) moiety retaining its NSAID activity can be synthesized by reaction of amines with NO in a solvent such as ether in the presence of a base such as sodium ethoxide to provide the NO-adduct. The NO adduct can be reacted with for example chloromethylmethylsulfide, which reacts with for example sulfuryl chloride in a solvent such as dichloromethane to provide the chloromethyl intermediate. The chloromethyl intermediate can be reacted with for example a carboxyl group to provide the substituted diazene-1-ium-1,2-diolates.

The invention also provides a pharmaceutical composition comprising (a) the compound of formula (I) or a salt thereof and (b) a pharmaceutically acceptable carrier. In the pharmaceutical compositions described herein, any suitable pharmaceutically acceptable carrier can be used, and such carriers are well known in the art. The choice of carrier will be determined, in part, by the particular site to which the pharmaceutical composition is to be administered and the particular method used to administer the pharmaceutical composition.

Suitable formulations include aqueous and non-aqueous solutions, isotonic sterile solutions, which can contain antioxidants, buffers, bacteriostats, and solutes that render the formulation isotonic with the blood or other bodily fluid of the intended recipient, and aqueous and non-aqueous sterile suspensions that can include suspending agents, solubilizers, thickening agents, stabilizers, and preservatives. In one embodiment, the pharmaceutically acceptable carrier is a liquid that contains a buffer and a salt. The formulation can be presented in unit-dose or multi-dose sealed containers, such as ampoules and vials, and can be stored in a freeze-dried (lyophilized) condition requiring only the addition of the sterile liquid carrier immediately prior to use. Extemporaneous solutions and suspensions can be prepared from sterile powders, granules, and tablets. In one embodiment, the pharmaceutically acceptable carrier is a buffered saline solution.

Further carriers include sustained-release preparations, such as semipermeable matrices of solid hydrophobic polymers containing the active agent, which matrices are in the form of shaped articles (e.g., films, liposomes, or microparticles). Alternatively, a delayed release formulation, including an enteric coating comprising a compound of formula (I) or a salt thereof, can be prepared.

The pharmaceutical composition can include carriers, thickeners, diluents, buffers, preservatives, surface active agents, and the like. The pharmaceutical compositions can also include one or more additional active ingredients, such as antimicrobial agents, anti-inflammatory agents, anesthetics, and the like.

The pharmaceutical composition comprising the compound of formula (I) or a salt thereof can be formulated for any suitable route of administration, depending on whether local or systemic treatment is desired, and on the area to be treated. The pharmaceutical composition can be formulated for parenteral administration, such as intravenous, intraperitoneal, intrathecal, intraarterial, subcutaneous, intramuscular, or intratumoral injection. Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier immediately prior to use. Extemporaneous injection solutions and suspensions can be prepared from sterile powders, granules, and tablets of the kind previously described.

The pharmaceutical composition comprising the compound of formula (I) or a salt thereof can be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

The pharmaceutical composition also can be administered orally. Oral compositions can be in the form of powders or granules, suspensions or solutions in water and/or non-aqueous media, capsules, pills, sachets, or tablets. Thickeners, flavorings, diluents, emulsifiers, dispersing aids, or binders may be desirable.

If desired, tablets or pills can be coated with a sugar coating, or a gastric or enteric coating agent. The term "enteric coating" means a coating or barrier applied to a dosage form that can control the location in the digestive system where the compound of formula (I) or a salt thereof is absorbed. For example, an enteric coating can be used to protect the drug from the destructive action of the enzymes or low pH environment of the stomach. In certain embodiments, the enteric coated dosage form can be regarded as a type of delayed release dosage form. Enteric coatings work by presenting a surface that is substantially stable at acidic pH, but breaks down at higher pH to allow release of the drug in the intestine.

An enteric coating can comprise an enteric polymer, which is a polymeric substance that when used in an enteric coating, is substantially insoluble and/or substantially stable under acidic conditions exhibiting a pH of less than about 5 and which is substantially soluble or can decompose under conditions exhibiting a pH of about 5 or more. Non-limiting examples of such enteric polymers include carboxymethylethylcellulose, cellulose acetate phthalate, cellulose acetate succinate, methylcellulose phthalate, hydroxymethylethylcellulose phthalate, hydroxypropylmethylcellulose phthalate, hydroxypropylmethylcellulose acetate succinate, polyvinyl alcohol phthalate, polyvinyl butyrate phthalate, polyvinyl acetal phthalate, a copolymer of vinyl acetate/maleic anhydride, a copolymer of vinylbutylether/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate and mixtures thereof. Enteric polymers can be used individually or in combination with other hydrophobic or hydrophilic polymers in an enteric coating. Enteric polymers can be combined with other pharmaceutically acceptable excipients to either facilitate processing of a coat comprising the enteric polymer or to alter the functionality of the coating.

Additionally, the compound of formula (I) or a salt thereof can be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable carriers and their formulations are further described in A. R. Gennaro, ed., *Remington: The Science and Practice of Pharmacy* (19th ed.), Mack Publishing Company, Easton, Pa. (1995).

The compound or a pharmaceutical composition comprising at least one compound of formula (I) or a salt thereof can be administered in or on a device that allows controlled or sustained release of the compound of formula (I) or a salt thereof, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the active agents. The pharmaceutical compositions of the inventive method also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid. Of course, administration of the compound or pharmaceutical composition can be accomplished via any route that efficiently delivers the active agents to the target tissue.

The inventive methods comprise administering an effective amount of a compound of formula (I) or a salt thereof. An "effective amount" means an amount sufficient to show a meaningful benefit in an individual, e.g., reducing the adverse effects of, treatment, healing, prevention, delay of onset, or amelioration of other relevant medical condition(s) associated with a particular disorder (e.g., a cardiovascular disorder). Preferably, one or more symptoms of the disorder are prevented, reduced, or eliminated subsequent to administration of a compound of formula (I) or a salt thereof, thereby effectively treating the disorder to at least some degree.

Effective amounts may vary depending upon the biological effect desired in the individual, condition to be treated, and/or the specific characteristics of the compound of formula (I) or a salt thereof, and the individual. In this respect, any suitable dose of the compound of formula (I) or a salt thereof can be administered to the patient (e.g., human), according to the type of disorder to be treated. Various general considerations taken into account in determining the "effective amount" are known to those of skill in the art and are described, e.g., in Gilman et al., eds., Goodman And Gilman's: *The Pharmacological Bases of Therapeutics*, 8th ed., Pergamon Press, 1990; and Remington's Pharmaceutical Sciences, 17th Ed., Mack Publishing Co., Easton, Pa., 1990, each of which is herein incorporated by reference. The dose of the compound of formula (I) or a salt thereof desirably comprises about 0.1 mg per kilogram (kg) of the body weight of the mammal (mg/kg) to about 400 mg/kg (e.g., about 0.75 mg/kg, about 5 mg/kg, about 30 mg/kg, about 75 mg/kg, about 100 mg/kg, about 200 mg/kg, or about 300 mg/kg). In another embodiment, the dose of the compound of formula (I) or (II) comprises about 0.5 mg/kg to about 300 mg/kg (e.g., about 0.75 mg/kg, about 5 mg/kg, about 50 mg/kg, about 100 mg/kg, or about 200 mg/kg), about 10 mg/kg to about 200 mg/kg (e.g., about 25 mg/kg, about 75 mg/kg, or about 150 mg/kg), or about 50 mg/kg to about 100 mg/kg (e.g., about 60 mg/kg, about 70 mg/kg, or about 90 mg/kg).

For purposes of the present invention, the term "patient" preferably is directed to a mammal. Mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human.

The invention further provides a method of treating a disorder in a patient comprising administering an effective amount of a compound of formula (I) or a salt thereof, wherein the disorder is a cardiovascular disorder, cancer, chronic pain, alcohol dependence, or inflammation. Preferably, one or more symptoms of the disorder are prevented, reduced, or eliminated subsequent to administration of the compound of the invention, thereby effectively treating or preventing the disease to at least some degree.

The cardiovascular disorder can be, for example, coronary artery disease, aneurysm, arteriosclerosis, atherosclerosis (including atherosclerotic plaque rupture and cardiac transplant atherosclerosis), myocardial infarction, hypertension, ischemia, embolism, stroke, thrombosis (including venous thrombosis), thromboembolism, restenosis, angina, shock, or chronic or acute heart failure.

Cancers treatable with the methods described herein include tumors associated with the oral cavity (e.g., the tongue and tissues of the mouth) and pharynx, the digestive system (e.g., the esophagus, stomach, small intestine, colon, rectum, anus, liver, gall bladder, and pancreas), the respiratory system (e.g., the larynx, lung, and bronchus), bones and joints (e.g., bony metastases), soft tissue, the skin (e.g., melanoma and squamous cell carcinoma), breast, the genital system (e.g., the uterine cervix, uterine corpus, ovary, vulva, vagina, prostate, testis, and penis), the urinary system (e.g., the urinary bladder, kidney, renal pelvis, and ureter), the eye and orbit, the brain and central nervous system (CNS) (e.g., glioma), and the endocrine system (e.g., thyroid). The target tissue also can be located in lymphatic or hematopoietic tissues. For example, the tumor can be associated with lymphoma (e.g., anaplastic large-cell lymphoma, Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like). The tumor to be treated is not necessarily the primary tumor. Indeed, the tumor can be a metastasis of a primary tumor located in a different tissue or organ.

Specific examples of cancers treatable with the present methods include, without limitation, adrenocortical carcinoma, AIDS-related lymphoma, AIDS-related malignancies, anal cancer, cerebellar astrocytoma, bile duct cancer (e.g., extrahepatic bile duct cancer), bladder cancer, osteosarcoma/ malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, eye cancers, including intraocular melanoma, and retinoblastoma, gallbladder cancer, gastrointestinal carcinoid tumor, gastrointestinal stromal cancer, ovarian germ cell tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, liver cancer, non-small cell lung cancer, small cell lung cancer, non-Hodgkin's lymphoma, Waldenstrom's macroglobulinemia, malignant mesothelioma, malignant thymoma, medulloblastoma, melanoma, intraocular melanoma, merkel cell carcinoma, metastatic squamous neck cancer with occult primary, multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (e.g. renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodermal and pineal tumors, cutaneous t-cell lymphoma, testicular cancer, malignant thymoma, thyroid cancer, gestational trophoblastic tumor, urethral cancer, uterine sarcoma, vaginal cancer, vulvar cancer, and Wilms' tumor. See, e.g., *Harrison's Principles of Internal Medicine*, Eugene Braunwald et al., eds., pp. 491-762 (15th ed. 2001).

In an embodiment of the methods of the invention, the cancer is leukemia, thyroid cancer, colon cancer, melanoma, renal cancer, prostate cancer, breast cancer, lung cancer, non-small cell lung cancer, liver cancer, pancreatic cancer, or ovarian cancer.

Chronic pain can be caused by any underlying condition or disorder, such as neuropathic pain conditions, diabetic peripheral neuropathy, post-herpetic neuralgia, trigeminal neuralgia, post-stroke pain syndromes, or cluster or migraine headaches.

Alcohol dependence includes alcoholism and alcohol abuse.

Inflammation can be acute inflammation or chronic inflammation. Inflammation can be, but is not necessarily, caused by or associated with any number of conditions, including asthma, an autoimmune disease (e.g., diabetes mellitus type 1), inflammatory bowel disease, pelvic inflammatory disease, reperfusion injury, rheumatoid arthritis, and vasculitis. The inflammation also can be coronary plaque inflammation, bacterial-induced inflammation (e.g., Chlamydia-induced inflammation), viral induced inflammation, or inflammation associated with surgical procedures (e.g., vascular grafting, coronary artery bypass surgery, and revascularization procedures (e.g., angioplasty, stent placement, endarterectomy, and vascular procedures involving arteries, veins, and capillaries)).

In accordance with an embodiment of the invention, the nitroxyl donating compounds are administered prior to the onset of ischemia for the prevention and/or reduction of ischemia/reperfusion injury in subjects at risk for ischemia. Nitroxyl donors also are administered to organs to be transplanted for the prevention and/or reduction of ischemia/reperfusion injury upon reperfusion in a recipient. See, e.g., U.S. Patent Application Publications 2009/0246296 A1, 2005/0192254 A1, 2004/0039063 A1, and 2004/0038947 A1, the disclosures of which are totally incorporated herein by reference.

In accordance with an embodiment of the invention, the compound of formula (I) or a salt thereof is administered under conditions where HNO is released in a greater quantity than NO. Preferably, the compound of formula (I) or a salt thereof releases substantially all HNO under physiological conditions. The term "substantially" means the compound of formula (I) or a salt thereof releases at least about 50% HNO (e.g., at least about 55%, at least about 60%, at least about 65%, at least about 70%, at least about 75%, at least about 80%, at least about 85%, at least about 90%, at least about 95%, or actually about 100%). The production of HNO and/or NO can be measured by methods described herein.

In an embodiment of the invention, an esterase inhibiting compound is co-administered with the compound of formula (I) or a salt thereof. Co-administration can be simultaneous, sequential or in parallel, or cyclic. With parallel administration, the compound of formula (I) or salt thereof and the esterase inhibiting compound can be administered in either order.

The following examples further illustrate the invention but, of course, should not be construed as in any way limiting its scope.

EXAMPLES

Unless otherwise noted, chemicals were purchased from Sigma-Aldrich and were used without further purification. IPA/NO (Na[(CH$_3$)$_2$CHNH(N(O)NO], sodium 1-(N-isopropylamino)diazen-1-ium-1,2-diolate, 1) was synthesized and utilized as previously described (Drago et al., *J. Am. Chem. Soc.*, 83: 1819-1822 (1961); Maragos et al., *J. Med. Chem.*, 34: 3242-3247 (1991)). Purity was confirmed spectrally at 250 nm ($\epsilon$ 10 mM$^{-1}$ cm$^{-1}$). (Miranda et al., *J. Med. Chem.*, 48: 8220-8228 (2005)). The concentrations of stock solutions (>10 mM), prepared in 10 mM NaOH and stored at −20° C., also were determined directly prior to use from the absorbance at 250 nm.

Example 1

This example demonstrates a method of synthesis of O$^2$-(acetoxymethyl) 1-(isopropylamino)diazen-1-ium-1,2-diolate (AcOM-IPA/NO) (2) in accordance with an embodiment of the invention.

A solution of bromomethyl acetate (867 mg, 5.67 mmol) in 3 mL of THF was reacted with a slurry of IPA/NO (800 mg, 5.67 mmol, in 10 mL of DMSO) at room temperature. The reaction mixture was stirred overnight whereupon 15 mL of water is added and stirring was continued for another 10 min. The residue was extracted with dichloromethane, washed with 5% sodium bicarbonate, dried over anhydrous sodium sulfate, filtered, and evaporated in vacuo to give a colorless oil. Column chromatography was performed using hexane:acetone (4:1) to give the desired product 2 (880 mg, 81%): UV (ethanol) $\lambda_{max}$ ($\epsilon$) 240 nm (8.7 mM$^{-1}$ cm$^{-1}$); NMR (CDCl$_3$) δ 1.19 (d, J=6.4 Hz, 6H), 2.12 (s, 3H), 4.00 (sept, J=6.4 Hz, 1H), 5.75 (s, 2H), 6.25 (d, J=9.1 Hz, 1H); $^{13}$C NMR (CDCl$_3$) δ 20.34, 20.81, 49.17, 87.07, 169.42. Anal. Calcd for C$_6$H$_{13}$N$_3$O$_4$: C, 37.69; H, 6.85; N, 21.98. Found: C, 37.77; H, 6.98; N, 21.82.

Example 2

This example illustrates kinetic studies of AcOM-IPA/NO (2) prepared in Example 1 in accordance with an embodiment of the invention.

The rate constants of decomposition were measured spectrophotometrically by monitoring the decrease in absorbance of peaks at ~240-250 nm characteristic of the diazeniumdiolate functionality. The hydrolysis medium consisted of the metal chelator diethylenetriaminepentaacetic acid (DTPA, 50 μM) in calcium- and magnesium-free Dulbecco's phosphate-buffered saline (PBS, pH 7.4). UV-visible spectroscopy was performed with a Hewlett-Packard 8453 diode-array spectrophotometer equipped with Agilent 89090A thermostat set to 37° C. The spectrophotometer was blanked after warming the cuvette containing buffer at the appropriate pH in the instrument heat block for 5 min. For esterase-containing reactions, porcine liver esterase (20 μL; Sigma; suspension in 3.2 M (NH$_4$)$_2$SO$_4$, pH 8) was added to the reaction buffer before blanking. Upon addition of IPA/NO (1) or AcOM-IPA/NO (2) (≤10 μL of stock), the cuvette was capped and inverted to mix. Spectra were collected at 0.5- to 60-s intervals for time periods of 2-120 min or until A$_\infty$<0.05. Kinetic analysis was performed by fitting the data to an exponential decay (A=ΔAe$^{-kt}$+A$_\infty$) using KaleidaGraph v.3.1.

Example 3

This example illustrates reductive nitrosylation of metmyoglobin by AcOM-IPA/NO (2) prepared in Example 1 in accordance with an embodiment of the invention.

To determine whether the products of hydrolyzing 2 include HNO, a method of trapping it with metmyoglobin (metMb) according to Equation 1 was established. This reductive nitrosylation reaction was followed spectrophotometrically by monitoring the decrease in metMb absorbance at 502 nm and the simultaneous increases in the peaks at 543 and 575 nm for MbNO.

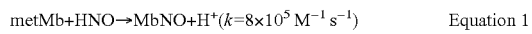

metMb+HNO→MbNO+H$^+$ ($k$=8×10$^5$ M$^{-1}$ s$^{-1}$)      Equation 1

Reductive nitrosylation of ferric myoglobin (metMb) to nitrosyl myoglobin (MbNO) by 1 or 2 was monitored in a quartz cuvette in assay buffer at 37° C. Formation of HNO was further examined by quenching with GSH, which does not interact directly with low concentrations of NO. To maintain deaerated conditions, all solutions were transferred using gas-tight Hamilton syringes, and the reaction buffer was sparged with ultra-high purity argon at the rate of 1 min for each mL of buffer. Aliquots (2-3 mL) were removed by Hamilton syringe and transferred to an argon-flushed, graded seal quartz cuvette (Spectrocell; Oreland, Pa.) stoppered with a Suba-Seal septum (Sigma-Aldrich). The buffer within the cuvette was again gently bubbled with argon for 5 min. In a separate stoppered vial, a small amount of horse heart myoglobin was purged with argon for 15 min while in an ice bath and then dissolved with deaerated buffer. An aliquot of metMb (>1 mM stock; A$_{502}$=10.2 mM$^{-1}$ cm$^{-1}$) was added by syringe, as were aliquots of GSH (approximately 100×; 250 μM final) as appropriate. The reaction was initiated by introducing a small volume of stock diazeniumdiolate solution (1 in 10 mM NaOH, 2 in methanol, kept on ice; 100 μM final) to the metMb (50 μM final) solution. Spectra were collected at 30- to 60-s intervals for 60-90 min or until A$_{543}$ and A$_{575}$ reaches stable values. The concentration of MbNO was determined spectrophotometrically (A$_{543}$=11.6 mM$^{-1}$ cm$^{-1}$; A$_{575}$=10.5 mM$^{-1}$ cm$^{-1}$ (Antonini and Brunori, *Frontiers Biol*, 21, 19 (1971)); or in case of incomplete conversion A$_{575}$=5.2 mM$^{-1}$ cm$^{-1}$; A$_{575}$=6.7 mM$^{-1}$ cm$^{-1}$).

Figure 1B:
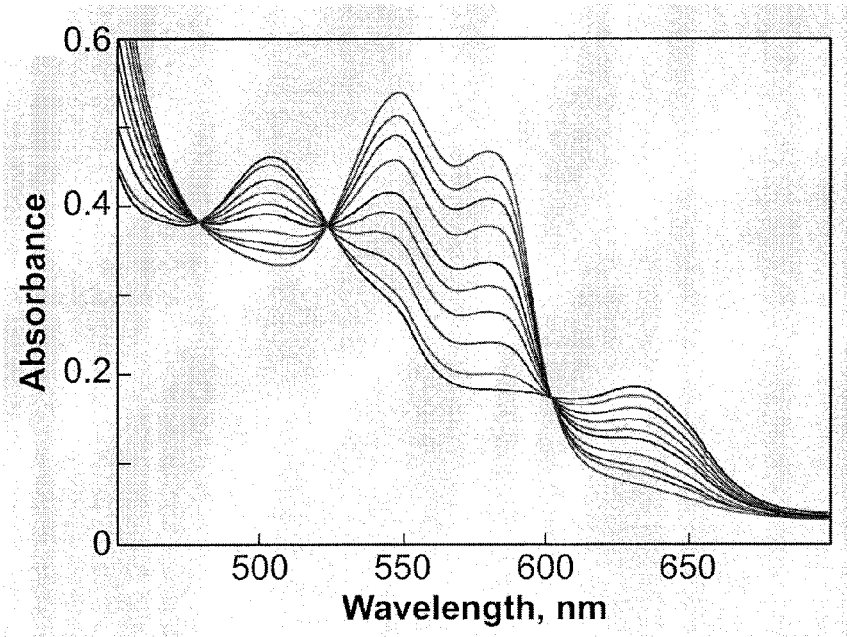

As shown in FIGS. 1A and 1B, both 1 (FIG. 1A) and 2 (FIG. 1B) at 100 μM concentration converted 50 μM metMb to MbNO, but 2 did so more efficiently, the yields being approximately 25 μM and 47 μM out of a possible 50 μM, respectively.

Figure 2A:
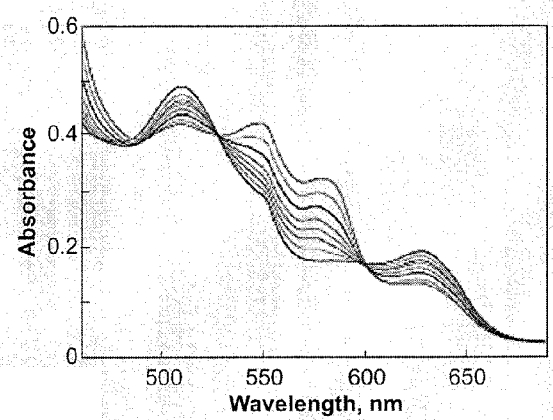
FIGS. 2A-D are graphs illustrating the effect of glutathione (GSH) on the reductive nitrosylation of metMb (50 μM) by (FIG. 2A) 1 (100 μM), (FIG. 2B) 2 (100 μM), (FIG. 2C) DEA/NO (50 μM), or (FIG. 2D) Angeli's salt (100 μM). The assay was performed in PBS (pH 7.4) containing 50 μM DTPA and 250 μM GSH at 37° C. under deaerated conditions over 1 h at 30-s cycles for 1 and 1.8 h at 30-s intervals for 2. Scans were plotted in FIG. 2A at 2, 4, 6, 9, 14, 23 and 56 min for 1. Scans were plotted in FIG. 2B at 0.5 and 60 min for 2. Scans were plotted in FIG. 2C at 1-min intervals to 8 min and then at 11, 14, 18, 23, 28 and 40 min. Scans were plotted in FIG. 2D at 500 s, when the decomposition of Angeli's salt was complete, and at 60 min, respectively.
Figure 2B:
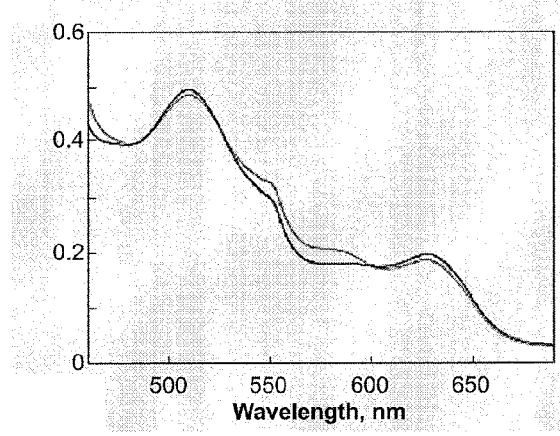
Figure 2C:
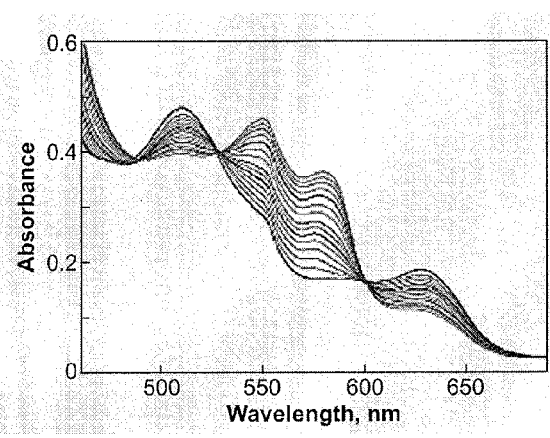
Figure 2D:
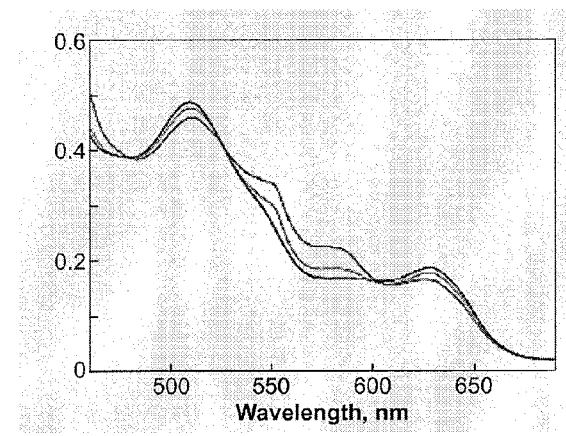

To confirm the production of nitroxyl in the spontaneous hydrolysis of 2, the reactions described above were repeated but in the presence of excess glutathione (GSH). GSH reacts 10-fold more rapidly than metMb with HNO but does not interact appreciably with low concentrations of NO. As seen in FIG. 2B, under deaerated conditions GSH inhibited reductive nitrosylation by 2 as expected based on the respective rate constants. Interestingly, GSH enhanced the formation of MbNO during the hydrolysis of 1 under these conditions (FIG. 2A). It was speculated that this was because 1 hydrolyzes to produce both HNO and NO. In deaerated solution, the NO coordinated weakly with metMb to form metMbNO, which was then reduced by GSH to MbNO (Reichenbach et al, *Nitric Oxide*, 5, 395-401 (2001)). FIG. 2A shows spectral changes comparable to those observed when the "pure" NO donor DEA/NO is hydrolyzed in the presence of both metMb and GSH (FIG. 2C). In contrast, the reaction of 2 with metMb in the presence of GSH was similar to that of the "pure" HNO donor Angeli's salt (FIG. 2D), confirming that 2 is similar to Angeli's salt in its HNO-generating ability.

Example 4

This example illustrates the analysis of products formed during hydrolysis of O$^2$-(acetoxymethyl) 1-(isopropylamino) diazen-1-ium-1,2-diolate (AcOM-IPA/NO) (2) in accordance with an embodiment of the invention.

In addition to HNO measurements as described above by reductive nitrosylation of metmyoglobin, NO was quantified by chemiluminescence assay, N$_2$O by gas chromatography, and nitrite ion by the Griess assay.

Organic products of the hydrolysis of 1 and 2 were quantified by integrating their NMR spectra. For pH 7.4, 3.9 mM solutions in 0.1 M phosphate buffer were employed. For pH 11, 4.9 mM solutions of 1 and 2 in 50 mM sodium carbonate were studied. Samples were run on a Varian Inova 400 MHz NMR with a Dell Precision 390 workstation. The samples were run at 37° C. and water suppression was achieved by using the preset pulse sequence. Peaks were identified by comparison with authentic standards.

Authentic propene was produced as a reference for the identification of this gas as a product of the reactions by the following procedure. Isopropylamino methyl carbamate was dissolved in dichloromethane and extracted with an equivalent volume of 1 M hydrochloric acid. A solution of sodium nitrite in water was added gradually. The bottom yellow-green layer was separated, dried over sodium sulfate, and concentrated under vacuum. A portion of the resulting oil (~5 μL) was dissolved in 10% sodium deuteroxide in D$_2$O and allowed to decompose for 1 h. The NMR spectrum exhibited signals corresponding to methanol, isopropanol, starting carbamate, and a small (presumably saturating) concentration of propene. Its methyl group signals appeared as a doublet of triplets (δ 1.70 and 1.72, J=1.5 and 6.5 Hz) identical to those observed in the hydrolysis of 1 and 2.

Compound 1 produced both NO and HNO on spontaneous hydrolysis at neutral pH. Surprisingly, the total amount of NO detected on hydrolyzing 2, a compound of formula (I), under the same conditions while purging gases formed in the reaction into an NO-specific chemiluminescence detector, was less than 1% of theoretical yield.

Figure 3A:
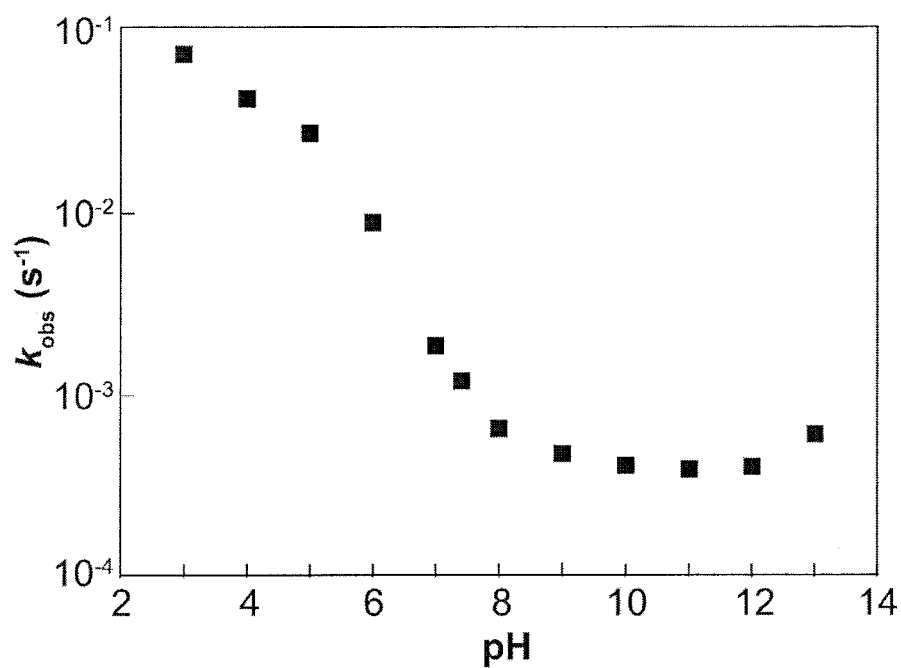
FIGS. 3A and 3B are graphs illustrating the pH-dependence of the rate constant of decomposition of (FIG. 3A) 1 (100 or 200 μM) and (FIG. 3B) 2 (100 μM) at 37° C. in PBS containing 50 μM DTPA measured at 250 nm (mean±SEM, n≥3).
Figure 3B:
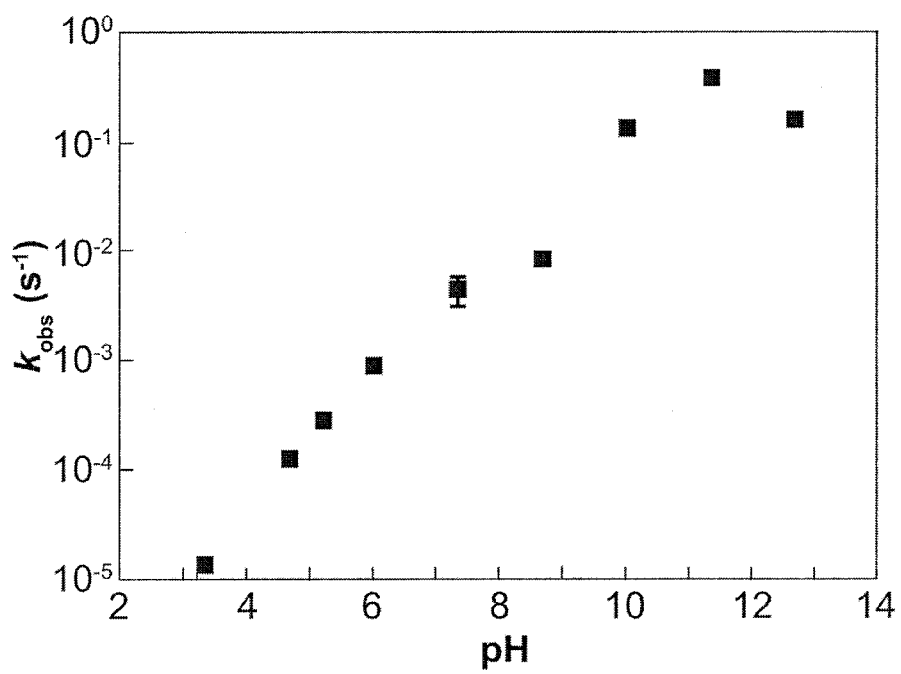

To gain insight into the mechanistic origins of this unexpected finding, the pH/rate profiles of the diazeniumdiolates 1 and 2 were explored. As previously established and shown in FIG. 3A, hydrolysis of 1 slowed as the pH was increased from 3 to 10, with a small increase in rate thereafter. This was the opposite of the results with 2, whose hydrolysis rate was essentially first order in hydroxide ion concentration between pH 5 and 11 (FIG. 3B).

Figure 4A:
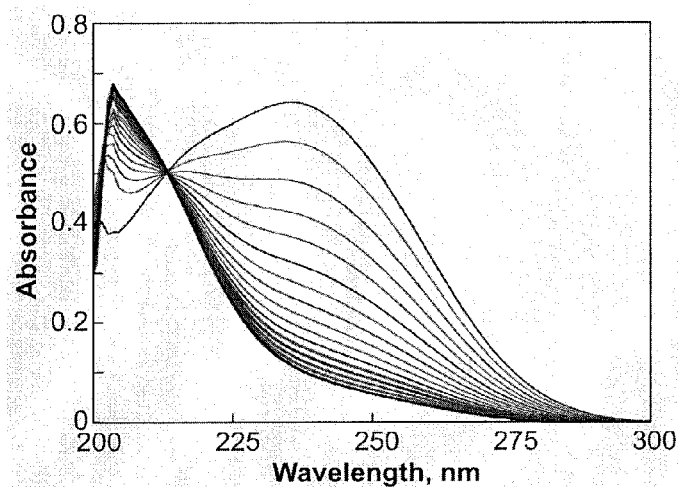
FIGS. 4A-C are graphs illustrating spontaneous hydrolysis (FIGS. 4A and 4B) and esterase-catalyzed hydrolysis (FIG. 4C) of 2 in an embodiment of the invention.
Figure 4B:
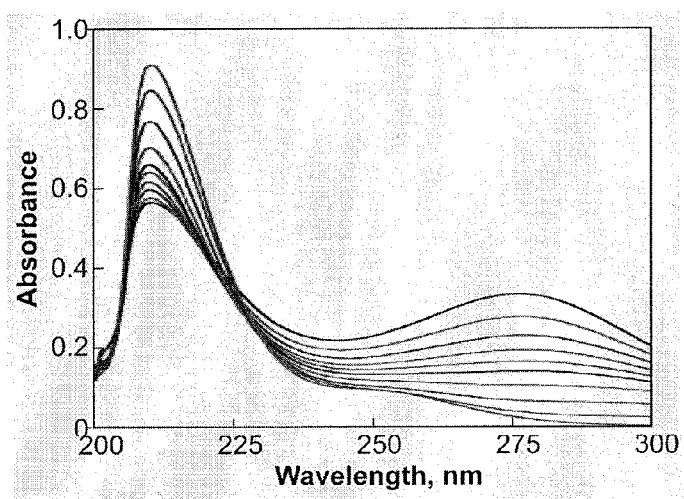

At and above pH 8, the rate of decomposition of 2 exceeds that of 1 (FIG. 3B versus FIG. 3A), indicating a mechanism involving more than simple hydrolysis of 2 to 1. Correspondingly, ultraviolet absorbance at 250 nm due to 1 was not observed in the spontaneous hydrolysis of 2 at pH 7.4 (FIG. 4A). Of further importance, there was a shift in ultraviolet maximum for 2 from $\lambda_{max}$ 236 nm to $\lambda_{max}$ 278 nm as the pH is raised to 12. This result is consistent with ionization of the N—H bond (FIG. 4B).

Figure 4C:
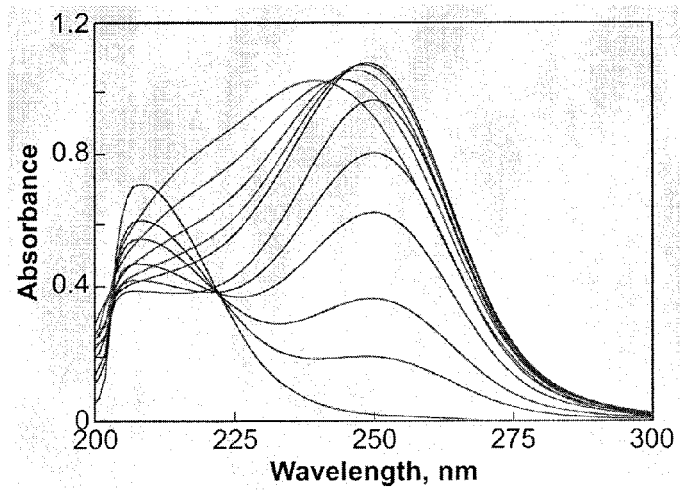

In contrast to simple buffer solutions, 1 is an observable intermediate in the hydrolysis of 2 when active esterase is present. As shown in FIG. 4C, the 250-nm peak for 1 dominated the spectrum within a short time after adding the enzyme to 2 in 0.1 M phosphate at pH 7.4. Additional studies confirmed that the esterase did not affect the stability of 1 or the ability of metMb and GSH to trap the hydrolytically produced HNO.

Consistent with the HNO/NO yield data, complete dissociation of 1 in pH 7.4 buffer showed it to generate similar amounts of isopropylamine and isopropanol, with essentially saturating concentrations of propene also being seen by NMR. In contrast, methyl peaks attributable to the amine border on undetectable in NMR spectra when 2 was hydrolyzed.

Differences in time course as well as stoichiometry in the alkaline hydrolysis of 1 and 2 also matched the expectation based on the HNO/NO yield and rate data. Ionic 1 hydrolyzed slowly at pH 11, and isopropylamine was not detected among the products, which is consistent with the spectral findings described above. Compound 2, on the other hand, completely dissociated within 5 min at 37° C. in a pH 11 carbonate buffer. Peaks for formaldehyde and acetate ion were seen in addition to those for the carbocation-derived alcohol and alkene. However, the amine was undetectable.

Without wishing to be bound by any theory, one way to rationalize the absence of free 1 as a hydrolysis product is that base-induced removal of the N—H proton of 2 generated intermediate ion 3', which might be expected to undergo 1-4 acyl migration via cyclic intermediate 4' as shown in the following scheme. Expulsion of formaldehyde from 4' could give 5', which could then fragment with N—N bond cleavage to produce diazoate ion 6' and acylnitroso derivative 7'. Aliphatic diazoates are known progenitors of "hot" carbenium ions that can indiscriminately alkylate ambient nucleophiles (such as water to produce the corresponding alcohol) with cogeneration of an equivalent of dinitrogen, and acylnitroso compounds such as 7' are known to hydrolyze to HNO with the derived carboxylate as by-product.

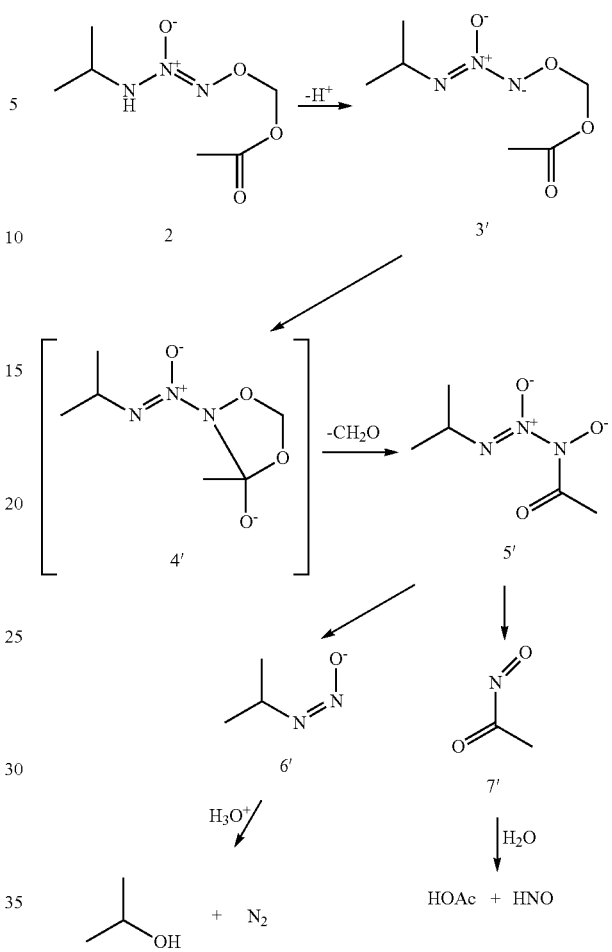

Example 5

This example demonstrates the effects of $O^2$-(acetoxymethyl) 1-(isopropylamino)diazen-1-ium-1,2-diolate (AcOM-IPA/NO) (2) on cardiac myocytes in accordance with an embodiment of the invention.

A stock solution of 2 in DMSO was freshly prepared prior to each experiment and stored on ice protected from the light. Liberase blendzyme 3 was purchased from Roche Diagnostics (Mannheim) while $CaCl_2$, DMSO, and glucose were purchased from Merck (Darmstadt). Calcium-free perfusion buffer contained 113 mM NaCl, 4.7 mM KCl, 0.6 mM $KH_2PO_4$, 0.6 mM $Na_2HPO_4$, 1.2 mM $MgSO_4$, 12 mM $NaHCO_3$, 10 mM $KHCO_3$, 30 mM taurine, 5.5 mM glucose, 10 mM 2,3-butanedione monoxime, and 10 mM 4-(2-hydroxyethyl)-1-piperazineethanesulfonic acid (HEPES) at pH 7.4. Digestion buffer contained an additional 0.1 mg/mL of recombinant collagenases/proteases (Liberase blendzyme 3) and 12.5 µM $CaCl_2$. IonOptix solution for the sarcomere shortening measurements contained 135 mM NaCl, 4.7 mM KCl, 0.6 mM $KH_2PO_4$, 0.6 mM $Na_2HPO_4$, 1.2 mM $MgSO_4$, 1.25 mM $CaCl_2$, 20 mM glucose, and 10 mM HEPES at pH 7.46.

C57BL/6 male mice (13-15 weeks) were used in the present study. Ventricular myocytes were isolated from wild type hearts using a modified protocol of O'Connell et al., (AfCS Research Reports, 1(5): 1-9 (2003)). Isolation and culture of adult mouse cardiac myocytes for signaling studies were available from O'Connell et al. Briefly, the thorax was opened and the aorta was cut about 2 mm from its entry into the heart. Then the heart was quickly excised, and the aorta was placed onto a cannula with two fine curve-tip forceps and tied with a thread. The cannulated heart was mounted on a temperature-controlled perfusion system and perfused for 8 min with a Calcium-free perfusion buffer before switching to the digestion buffer. After 8-10 min of digestion, the ventricles were removed and placed in a digestion buffer, and the tissue was dissociated using forceps. Further enzyme activity was inhibited by the addition of 5% fetal bovine serum. Debris was sedimented by gravity and the supernatant, containing the intact cardiac myocytes, was centrifuged. The pellet was resuspended in fresh buffer and $CaCl_2$ was slowly reintroduced to a final concentration of 1 mM. After further centrifugation, ionOptix buffer was added on the pellet and sarcomere shortening was assessed on field stimulation (1 Hz with 4-ms duration, 10 V) using a video-based sarcomere length detection system (IonOptix Corporation) at room temperature.

Figure 5:
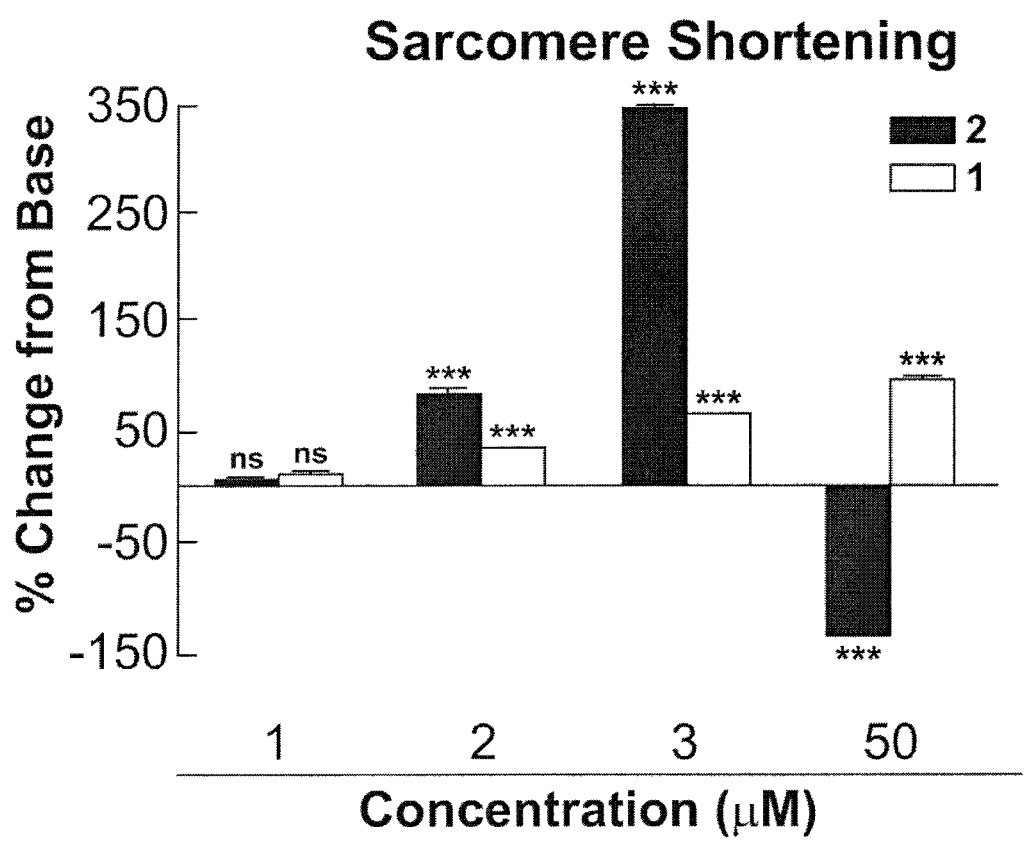
FIG. 5 is a graph illustrating the relative increases in contractility in isolated ventricular myocytes in an embodiment of the invention. Dose-response effects of 1 (white bars) and 2 (black bars) on sarcomere shortening are shown. ***P<0.001 vs. control. n=6 at 1 μM, 5 at 2 μM, and 15 for 3 and 50 μM.
Figure 6A:
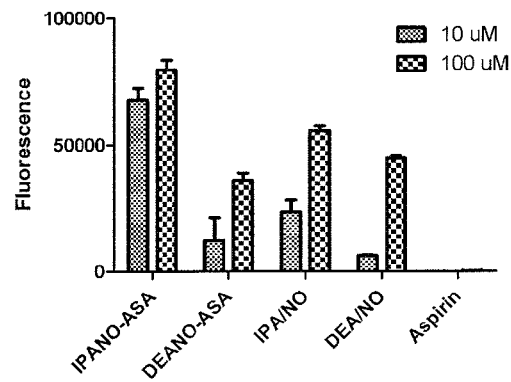
FIGS. 6A-6C are graphs illustrating NO and HNO release measured from reaction of 10 μM DAF-FM with 10 and 100 μM of DEA/NO-aspirin, IPA/NO-Aspirin and aspirin in DMSO (<0.1%) and IPA/NO and DEA/NO in 10 mM NaOH (FIG. 6A) without cells.
Figure 6B:
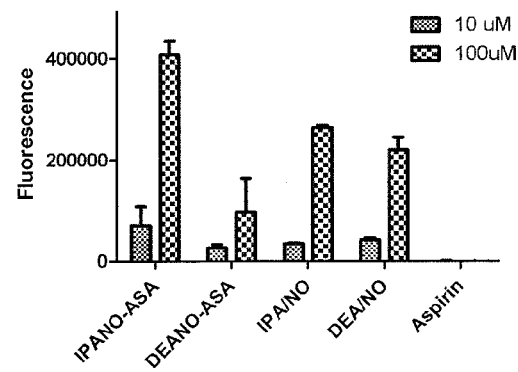
Figure 6C:
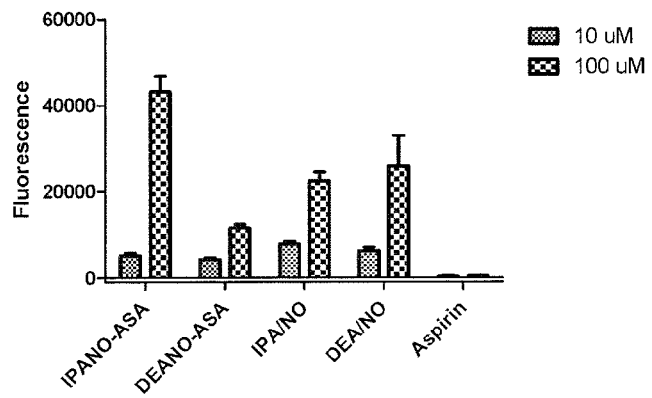

Compound 2, which is a compound of formula (I), proved more potent than compound 1 at micromolar concentrations in the isolated myocyte model of experimental heart failure. As shown in FIG. 5, 2 elicited an approximately 4-fold higher change than 1 in sarcomere shortening relative to baseline at 3 μM.

Example 6

This example demonstrates a method of synthesis of an embodiment of formula (I) wherein $R^4$ is an NSAID moiety: $O^2$-(Acetylsalicyloyloxymethyl)-1-(N-isopropylamino)-diazen-1-ium-1,2-diolate (IPA/NO-Aspirin; Compound 4). This example also demonstrate a method of synthesis of $O^2$-(Acetylsalicyloyloxymethyl)-1-(N,N-Diethylamino)-diazen-1-ium-1,2-diolate (DEA/NO-Aspirin; Compound 8).

IPA/NO-Aspirin 4 and DEA/NO-Aspirin 8 were synthesized via the following Scheme.

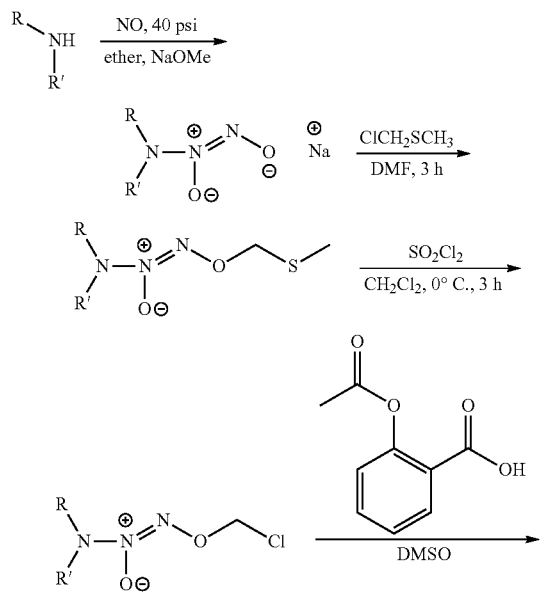

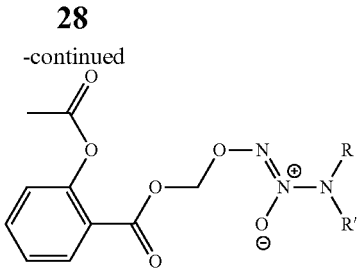

DEA/NO-Aspirin: R = R' = Et
IPA/NO-Aspirin: R = isopropyl; R' = H $O^2$-Sodium 1-(N-Isopropylamino)diazen-1-ium-1,2-diolate (1)

This compound was synthesized as described previously, Drago et al. and Margo et al. both supra $^1$H NMR (500 MHz, $CDCl_3$): δ 0.98 (d, J=6.5 Hz, 6H, $CH_3$), 4.06 (m, J=6.5 Hz, 1H, CH), 6.067 (s, 1H, NH). $^{13}$C NMR (500 MHz, $CDCl_3$): δ 21.343 ($CH_3$), 47.691 (CH).

$O^2$-(Methylthiomethyl)-1-(N-Isopropylamino)diazen-1-ium-1,2-diolate

Chloromethyl methyl sulfide (1.93 mL, 23.38 mmol) was added to a slurry solution of $Na_2CO_3$ (1.24 g, 11.69 mmol) in DMF (50 mL) at room temperature. Reaction mixture was stirred for 2 min before sodium salt of IPA/NO (3.297 g, 23.38 mmol) was added and stirring was continued for 3 h. Reaction mixture was quenched by addition of ethyl acetate (70 mL), which was then filtered and subsequently washed with 10% NaCl solution (5×40 mL). The organic layer was then dried over sodium sulfate and evaporated to obtain the crude product, which was further purified on flash column (20:80::EA: Hexane) to obtain (780 mg, 18.6%) of light yellow oil. $^1$H NMR (400 MHz, $CDCl_3$): δ 1.22 (d, J=6.5 Hz, 6H, $CH_3$), 4.06 (dq, J=6.5, 15.6 Hz, 1H, CH), 6.05 (d, J=9.1 Hz, 1H, NH), 5.24 (s, 2H, $CH_2$), 2.28 (s, 3H, $CH_3$). $^{13}$C NMR (500 MHz, $CDCl_3$): δ14.7 ($SCH_3$), δ19.96-20.006 ($CH_3$), δ48.789 (CH), δ78 ($CH_2SCH_3$). IR (NaCl): 3286, 3014, 2964, 1580, 1414, 1308, 1018, 976 (isopropyl amine portion and $CH_3SCH_2$ portion), 1170, 1133 (N=N—O). UV: ε ($λ_{213\ nm}$)=54.2 mM$^{-1}$ cm$^{-1}$, ($λ_{246\ nm}$)=7.24 mM$^{-1}$ cm$^{-1}$.

$O^2$-(Chloromethyl)-1-(N-Isopropylamino)diazen-1-ium-1,2-diolate

A solution of ($O^2$-(methylthiomethyl)-1-(N-isopropylamino)diazen-1-ium-1,2-diolate) (0.76 g, 4.25 mmol) dissolved in dichloromethane (17 mL) was cooled to −78° C. Then sulfuryl chloride (5 mL of 1.0 M solution in $CH_2Cl_2$, 4.67 mmol) was added drop-wise with stirring at 4° C. and the completion of the reaction was monitored by TLC. After 2 h, the reaction mixture was filtered and evaporated to yield yellow oil which was then used immediately for the next step without further purification. $^1$H NMR (500 MHz, $CDCl_3$): δ 1.22 (d, J=6.5 Hz, 6H, $CH_3$), 4.02 (m, J=6.5 Hz, 1H, CH), 6.23 (s, 1H, NH), 5.8 (s, 2H, $CH_2$). $^{13}$C NMR (500 MHz, $CDCl_3$): δ 20.393 ($CH_3$), δ49.373 (CH), δ79.254 ($CH_2Cl$).

$O^2$-(Acetylsalicyloyloxymethyl)-1-(N-isopropylamino)-diazen-1-ium-1,2-diolate

Aspirin (765 mg, 4.25 mmol) was dissolved in DMSO (2 mL). Triethylamine (0.6 mL, 4.25 mmol) was then added and the reaction mixture was stirred for 50 min at room temperature. Then a solution of $O^2$-(chloromethyl)-1-(N-isopropylamino)diazen-1-ium-1,2-diolate in DMSO (2 mL) was added drop wise to the reaction mixture. The reaction mixture was stirred for 15 h and after completion of the reaction; it was quenched with ethyl acetate (40 mL). The organic layer was washed with saturated $NaHCO_3$ solution (5×40 mL), dried over sodium sulfate and then evaporated to obtain the crude product. Further purification was performed by column chromatography (22% Ethyl Acetate:Hexane) to obtain IPA/NO-aspirin (460 mg, 37.8%) as viscous white oil. $^1$H NMR (500 MHz, $CDCl_3$): δ 1.16 [d, J=6.5 Hz, 6H, (CH3)2], 2.33 (s, 3H, COCH3), 3.98 (dq, J=6.5, 15.6 Hz, 1H, CH), 5.94 (s, 2H, OCH2O), 6.16 (d, J=9.25 Hz, 1H, NH), 7.1 (dd, J=8 Hz, 1 Hz, phenyl H-3), 7.3 (td, J=3 Hz, 1 Hz, phenyl H-5), 7.6 (td, J=3.5 Hz, 1.5 Hz, phenyl H-4), 8.04 (dd, J=8 Hz, 1.5 Hz, phenyl H-6). $^{13}$C NMR (500 MHz, $CDCl_3$): δ 20.872 (COCH3), 21.4 [(CH3)$_2$], 49.65 (CH), 88.164 (CH2), 122.59 (aromatic C1), 124.34 (aromatic C3), 126.5 (aromatic C5), 132.5 (aromatic C6), 135.01 (aromatic C4), 151.479 (aromatic C2), 163.177 (C=O), 170.04 (OC=OCH3). IR: 3286, 3014 (C—H aromatic), 2923 (C—H aliphatic), 1739 (CO2), 1602 (CO2), 1247, 1190 (N=N—O) cm$^{-1}$. Elemental analysis (C13H17N3O6): C=50.16; H=5.50; N=13.50 (theoretical), C=49.92; H=5.42; N=13.42 (experimental), MS (LCQ, ESI ionization method): 334.1 (MNa$^+$ peak), UV: ε ($\lambda_{240\,nm}$)=7.87 mM$^{-1}$ cm$^{-1}$.

$O^2$-Sodium 1-(N,N-Diethylamino)diazen-1-ium-1,2-diolate

Diethylamine (10 mL, 0.05 mol) and sodium methoxide in methanol (12 mL in 25% methanol, 0.05 mol) was added to diethyl ether (150 mL) at room temperature. This reaction mixture was then flushed with argon for 10 min and then exposed to nitric oxide (40 psi) for 24 h. The solid precipitate formed was filtered and washed with diethyl ether to obtain $O^2$-Sodium 1-(N,N-Diethylamino)diazen-1-ium-1,2-diolate (7.2 g, 0.046 mol, 92.9%) as white solid. $^1$H NMR (500 MHz, $CDCl_3$): δ 0.95 [t, J=7.0 Hz, 6H, (CH$_3$)$_2$], 2.9 (q, 4H, CH$_2$). $^{13}$C NMR (500 MHz, $CDCl_3$):

$O^2$-(Methylthiomethyl)-1-(N,N-Diethylamino)diazen-1-ium-1,2-diolate

To a mixture of sodium carbonate (2.391 g, 22.56 mmol) and DMF (50 mL) was added chloromethyl methyl sulfide (1.862 mL, 22.56 mmol) and the reaction mixture was stirred at room temperature for 5 min. Then DEA/NO (3.5 g, 22.56 mmol) was added to the reaction mixture and stirring was continued for 3 h. The reaction mixture was quenched by addition of 70 mL ethyl acetate and filtered. The organic layer was washed with 10% NaCl solution (5×40 mL), dried over sodium sulfate and evaporated to obtain the crude product, which was further purified by silica gel column chromatography (20:80=EA: Hexane) to give (2.6 g, 59.6%, Rf=0.48) a light yellow oil. $^1$H NMR (500 MHz, $CDCl_3$): δ 1.09 (t, J=7 Hz, 6H, CH$_3$), 2.21 (s, 3H, SCH$_3$), 3.1 (q, J=7 Hz, CH$_2$), 5.274 (s, 2H, CH$_2$). $^{13}$C NMR (500 MHz, $CDCl_3$): δ 11.477 [(CH$_3$)$_2$], 15.118 (CH$_3$), 48.465 [(CH$_2$)$_2$], 78.322 (OCH$_2$S).

$O^2$-(Chloromethyl)-1-(N,N-Diethylamino)diazen-1-ium-1,2-diolate

O-methylthiomethyl DEA/NO (2.1 g, 10.87 mmol) was dissolved in DCM (120 mL) and the reaction mixture was cooled to 0° C. Sulfuryl chloride (0.883 mL, 10.87 mmol) was then added slowly to the reaction mixture using a dropping funnel. The completion of the reaction mixture was monitored by TLC. The reaction mixture was filtered and evaporated, which was then used for next step without further purification. $^1$H NMR (500 MHz, CD$_3$CN): δ 1.1 (t, J=7 Hz, 6H, CH$_3$), 3.3 (q, J=7 Hz, 4H, CH$_2$), 5.97 (s, 2H, CH$_2$). $^{13}$C NMR (500 MHz, CD$_3$CN): δ 11.676 (CH$_3$), 48.522 (CH$_2$), 80.946 (CH$_2$Cl).

$O^2$-(Acetylsalicyloyloxymethyl)-1-(N,N-Diethylamino)-diazen-1-ium-1,2-diolate

To a solution of O-acetylsalicylic acid (1.865 g, 10.35 mmol) in DMSO (20 mL), triethylamine (1.455 ml, 10.35 mmol) was added and the reaction mixture was stirred for 30 min at room temperature. O-Chloromethyl DEANO (1.880 g, 10.35 mmol) was then dissolved in DMSO (20 mL) and added to the reaction mixture drop-wise. After 8 h, the reaction was quenched with ethyl acetate (70 mL). The organic layer was washed with 10% NaCl solution 5 times and evaporated to get the crude product. The crude product was purified using column chromatography (30% ethyl acetate-hexane) to obtain 2.2 g (65.1%) of pure product. $^1$H NMR (500 MHz, $CDCl_3$): δ 1.08 [t, J=4.5 Hz, 6H, (CH$_3$)$_2$], 2.33 (s, 3H, COCH3), 3.2 (q, J=7 Hz, 4H, CH$_2$), 5.995 (s, 2H, OCH2O), 7.09 (dd, J=1, 8 Hz, phenyl H-3), 7.3 (td, J=1, 7.5 Hz, phenyl H-5), 7.6 (td, J=1, 8 Hz, phenyl H-4), 8.03 (dd, J=1, 8 Hz, phenyl H-6). $^{13}$C NMR (500 MHz, $CDCl_3$): δ 11.45 [(CH$_3$)$_2$], 20.994 (COCH3), 48.002 [(CH$_3$)$_2$], 87.905 (CH$_2$), 122.076 (aromatic C1), 123.985 (aromatic C3), 126.0 (aromatic C5), 131.597 (aromatic C6), 134.521 (aromatic C4), 151.119 (aromatic C2), 162.528 (C=O), 169.556 (OC=OCH3). Elemental analysis (C13H17N3O6): C=51.69; H=5.89; N=12.92 (theoretical), C=51.49; H=5.13; N=12.73 (experimental), MS (LCQ, ESI ionization method): 348.1 (MNa$^+$ peak).

Example 7

This example demonstrates the kinetic profile of NO and HNO release from HNO-releasing aspirin (IPA/NO-aspirin) and NO-releasing aspirin (DEA/NO-aspirin).

The newly synthesized HNO-releasing aspirin (IPA/NO-aspirin, 4) and NO-releasing aspirin (DEA/NO-aspirin, 8) were evaluated for the kinetic profile of NO and HNO release in buffer and cells. Both NSAID modified compounds (4 and 8) were found to be relatively stable in phosphate buffer pH 7.4 for several hours.

Example 8

This example demonstrates the release of HNO and NO from HNO-releasing aspirin (IPA/NO-aspirin) and NO-releasing aspirin (DEA/NO-aspirin).

The release of NO was evaluated using an NO specific electrode. The NO electrode was stabilized in phosphate buffer pH 7.4 containing 2% serum. Compounds 4 and 8 in DMSO were added and the NO signal was measured. The experiment was repeated in the presence of 1 mM sodium ferricyanide.

100 μM of compound 8 readily released NO in the presence of 2% serum while 100 μM of compound 4 showed significantly lower NO production. Since there is no direct method for detection of HNO, 1 mM ferricyanide solution was used, which converts HNO to NO that can then be detected using NO electrode.

In spite of the faster decomposition kinetics of compound 4, the amount of NO detected is half of compound 8. This is due to self consumption of HNO due to dimerization (k=8× $10^6$ $M^{-1}$ $s^{-1}$) and reaction of HNO with NO (k=6×$10^6$ $M^{-1}$ $s^{-1}$) (Shafirovich et al., PNAS 99: 7340-7345 (2002)) (Table 1).

TABLE 1

|  | [NO]pA |
|---|---|
| IPA/NO-Aspirin | 1000 |
| IPA/NO-Aspirin (+Ferricyanide) | 2100 |
| DEA/NO-Aspirin | 4600 |
| DEA/NO-Aspirin (+Ferricyanide) | 5000 |

The reaction of metmyoglobin (metMb) with HNO was used for detection of HNO. 4 on reaction with metMb in the presence of 2% guinea pig serum under physiological conditions underwent reductive nitrosylation, thereby indicating production of HNO. The release profile from both 4 and 8 was also studied using oxymyoglobin (oxyMb), which reacts with both NO and HNO. HNO production from 4 was further verified by reaction of oxyMb with 4 in the presence of 1 mM glutathione (GSH), a HNO scavenger.

Detection of HNO was also carried out using the chemiluminescence method in, 1 mM ferricyanide solution. Again 4 showed both NO and HNO release while 8 shows NO release.

Example 9

This example demonstrates the NO/HNO release profiles for compounds 4 and 8 within A549 cells (lung carcinoma cell line).

The intracellular NO and HNO were determined by using 4-amino-5-methylamino-2',7'-difluorofluorescein diacetate (DAF-FM diacetate) as the reporter molecule. Cells were plated at a concentration of 30,000 cells per well in a 96 cell plate and grown overnight. Then DAF-FM diacetate in DMSO was added to each well with a final concentration of 10 μM and incubated for 30 min. Each well was washed three times with PBS pH 7.4. The desired compound was then added and the fluorescence was measured at an excitation of 485 nm and emission of 535 nm using PerkinElmer HTS 7000 plate reader.

Both NO and HNO increased the fluorescence of DAF. The NO/HNO release profiles for compounds 4 and 8 within A549 cells were determined by loading the cells with DAF-FM diacetate, a cell permeable dye, which is cleaved by esterase to form DAF-FM and reacts with NO to form benzotriazole derivative with an excitation of 495 nm and emission of 515 nm (Kojima et al., Chemical & Pharm. Bulletin, 462 373-75 (1998)). The reaction of HNO with DAF-FM diacetate has been shown to produce a higher fluorescence as compared to NO with same excitation and emission (Espey et al., Free Radical Biology and Medicine 33(6):827-34 (2002)). Both 4 and 8 show temporal release in the presence and absence of cells. DAF-FM diacetate loaded A549 cells showed significantly higher fluorescence with 4 as compared to 8, again reiterating HNO release from IPA/NO-aspirin. Moreover, when DAF-FM diacetate is present both inside and outside the cells, the fluorescence intensity is ten times higher than that without cells. This indicates that despite some decomposition at pH 7.4, both 4 and 8 penetrate the cells where the ester bond is cleaved.

Example 10

This example demonstrates the effect of IPA/NO-aspirin and DEA/NO-aspirin on a normal endothelial cell line (HUVECs) and A549 lung carcinoma cell line.

Unlike IPA/NO and DEA/NO, both IPA/NO-aspirin and DEA/NO-aspirin permeated the cell membrane with minimal decomposition. This indicates compounds 4 and 8 have the ability to produce much higher NO/HNO flux at a given concentration as compared to the parent diazen-1-ium-1,2-diolate.

The effect of compounds 4 and 8 was studied on proliferation of A549 cells by 3-(4,5-Dimethylthiazol-2-yl)-2,5-diphenyltetrazolium bromide (MTT) assay. Cells were plated at a concentration of 10,000 cells per well in a 96 well plate and grown overnight. Then the cells were treated with different concentration of the compounds and controls for 48 h. After 48 h, a solution of 2 mg/ml MTT was added to each well and incubated for 1 hr. The media was then removed from each well and 100 μL DMSO was added to each well and the absorbance was recorded at 550 nm.

Compound 4 showed slightly higher toxicity than compound 8. No significant cell death was observed in MTT assay of these compounds on normal endothelial cell line (HUVECs).

Example 11

This example demonstrates that compound 4 inhibits GAPDH activity at micro-molar concentrations in lung cancer cells.

In an effort to decipher the mechanism of action of compounds 4 and 8, their effect on glyceraldehyde-3-phosphate dehydrogenase (GAPDH) activity was measured. GAPDH is a glycolytic enzyme which reversibly catalyzes the oxidation of D-glyceraldehyde-3-phosphate to 1,3-diphosphoglycerate. This method utilizes the conversion of $NAD^+$ to NADH by GAPDH in the presence of glyceraldehydes-3-phosphate and phosphate, which can be measured at an excitation of 560 nm and emission of 590 nm.

Cells were plated at a concentration of 30,000 cells per well and grown overnight. Then they were treated with 100 μM IPA/NO-aspirin and DEA/NO-aspirin for 1, 3, and 6 h followed by which 200 μL of KDalert lysis buffer was added to each well. The plate was incubated at 4° C. for 20 min to lyse the cells. Then 10 μL of cell lysate was transferred to a clean 96 well plate and 90 μL of KDalert mastermix was added to each well and fluorescence was measured at excitation of 540 nm and emission of 570 nm. GAPDH is an enzyme involved in cell death and oxidative stress, which possesses a sulfhydryl group at its active site that can be reversibly/irreversibly inhibited by HNO. It is also a critical glycolytic enzyme that can play an important role in cancer therapy as solid tumors are known to utilize glycolytic pathways even during normoxia to meet energy requirements (Gatenby et al., Nat. Rev. Cancer, 4(11):891099 (2004)). Thus, inhibition of GAPDH can diminish the ATP requirements of tumor cells. It has been shown that HNO can inhibit GAPDH irreversibly due to formation of sulfonamide (Lopez et al., Archives of Biochemistry and Biophysics, 442(1): 140-48 (2005)) and significantly decrease tumor size (Norris et al., Int. J. of Cancer, 122(8): 1905-10 (2008)).

Figure 7:
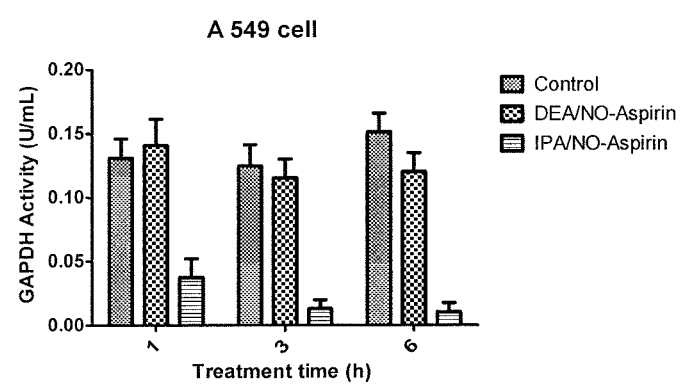
FIG. 7 is a graph showing the effect of 100 μM of DEA/NO-aspirin and IPA/NO-Aspirin in DMSO (<0.1%) on GAPDH activity in A549 cells at different time points.

Compound 4 showed inhibition of GAPDH activity at micro-molar concentrations, which further verifies HNO release (FIG. 7). HNO is known to inhibit GAPDH activity by sulfinamide formation at cysteine residue. Inhibition of GAPDH activity can be a key step towards anticancer activity of compound 4. Most tumor micro-environments are hypoxic in nature. Under inadequate supply of oxygen, cancer cells predominantly produce energy via anaerobic metabolism, which involve glycolysis followed by lactic acid fermentation in the cytosol, rather than aerobic citric acid cycle, i.e. oxidation of pyruvate in mitochondria like most normal cells. Thus, inhibition of GAPDH is a promising way to selectively target tumor cells. In spite of the change in GAPDH activity, no significant change was observed on mRNA levels of GAPDH.

Example 12

This example demonstrates that compound 4 decreases the amount of $PGE_2$ produced and compound 8 decreases $PGE_2$ level at lower concentrations.

Cells were plated at a concentration of 50,000 cells per well and grown overnight. Then 25, 50, and 100 μM of DMSO, IPA/NO-aspirin, and DEA/NO-aspirin were added to the corresponding well for 24 h and incubated at 37° C. The supernant was then analyzed for $PGE_2$ activity using prostaglandin E2 EIA kit (Cayman Cat No. 514010).

When the effect of compounds 4 and 8 was studied on $PGE_2$ production, compound 4 showed a significant decrease in the amount of $PGE_2$ produced, while 8 showed decreased $PGE_2$ level only at lower concentrations (Table 2).

TABLE 2

| Concentration (μM) | Prostaglandin $E_2$ (pg/ml) | |
| --- | --- | --- |
| | IPA/NO-ASA | DEA/NO-ASA |
| 0 | 33 | 33 |
| 25 | 17 | 21 |
| 50 | 14 | 38 |
| 100 | 13 | 36 |

Example 13

This example demonstrates that DEA/NO and DEA/NO-aspirin augment the effect of aspirin while IPA/NO and IPA/NO-aspirin nullifies the effect.

$PGE_2$ levels are a direct measure of COX-2 activity. COX-2 mRNA levels were also measured and 8 showed significant increase while 4 did not show much change with respect to the control. Increased COX-2 expression in the presence of aspirin has been reported previously (Davies et al., *Alimentary Pharm. & Ther.* 11(6):1101-08 (1997))). Both DEA/NO and DEA/NO-aspirin seem to augment the effect of aspirin while IPA/NO and IPA/NO-aspirin nullifies the effect and brings it back to the control level (Table 3).

TABLE 3

| | mRNA COX-1 |
| --- | --- |
| Control | 1.0 |
| Aspirin | 4.0 |
| IPANO-aspirin | 0.8 |
| DEANO-aspirin | 6.5 |
| IPA/NO | 1.2 |
| DEA/NO | 6.0 |

Example 14

This example demonstrates the in vivo anti-inflammatory activity of IPA/NO-aspirin and DEA/NO-aspirin.

Anti-inflammatory properties were studied in vivo in a carrageenan induced rat paw edema assay after 3 h of administration of the compound orally to Sprague-Dawley rats.

To verify whether IPA/NO-aspirin and DEA/NO-aspirin retain the anti-inflammatory properties of their parent NSAID in vivo, aspirin, PA/NO-aspirin or DEA/NO-aspirin was administered to rats with paw edema induced by carrageenan. IPA/NO-aspirin ($ID_{50}$=121.3 mg/kg) was found to be slightly more potent as compared to the parent drug while DEA/NO-aspirin ($ID_{50}$=168.6 mg/kg) was 1.3 times less potent (Table 4).

TABLE 4

| Treatment group | Anti-inflammatory Activity $ID_{50}$ (mg/kg) |
| --- | --- |
| IPA/NO-aspirin | 121.3 |
| DEA/NO-aspirin | 168.6 |
| Aspirin | 128.7 |

Example 15

This example demonstrates the ulcerogenicity property of a compound of the invention in accordance with an embodiment.

Ulcerogenicity was evaluated 6 h after oral administration of 250 mg/kg of aspirin (250 mg/kg) and an equivalent amount of the corresponding test compound. The compounds were suspended in 1.7 mL of a 1% methylcellulose solution and administered. The control rats received oral administration of a vehicle (1.7 mL of 1.0% methylcellulose solution). The rats were euthanized in a $CO_2$ chamber and their stomachs and placed on ice and then the ulcers were studied using magnifying glass. The ulcerogenicity was measured as ulcer index and the results are set forth in Table 5.

TABLE 5

| Treatment group | Ulcer Index (mg/kg) |
| --- | --- |
| IPA/NO-aspirin | 3.3 ± 3 |
| DEA/NO-aspirin | 0 |
| Aspirin | 57.4 ± 3.1 |

Both IPA/NO-aspirin (UI=3.0+3.0) and DEA/NO-aspirin (UI=0) showed substantially low ulcer index as compared to aspirin (UI=57.4) (Table 5).

Example 16

This example demonstrates that IPA/NO-aspirin and DEA/NO-aspirin reduce the survival of breast cancer cells more effectively than their parent compounds without affecting normal cells.

Cell Lines.

MDA-MB-231, MCF-7 and MDA-MB-468, human breast carcinoma cell lines and MCF-10A, breast endothelium (American Type Culture Collection, Manassas, Va.) were grown as monolayers in RPMI 1640 supplemented with 10% FCS (Hyclone), penicillin (50 units/ml), streptomycin (50 mg/ml; Life Technologies, Inc., Grand Island, N.Y.) and endothelial growth media (Lonanza) respectively. Cells were seeded at a density of $1\times10^6$ cells/100-$cm^2$ culture dish and incubated at 37° C. in 5% $CO_2$ and 80% relative humidity. Single-cell suspensions were obtained by trypsinization (0.05% trypsin/EDTA), and cells were counted using a Beckman cell counter.

1000× stock solutions aspirin, of a DEA/NO-ASA, and IPA/NO-ASA were made in DMSO and final concentration in the media or PBS was adjusted to 0.1% DMSO.

Compared to aspirin with $IC_{50}$ value in milli-molar range (Nath et al., *Biochemical Pharmacology*, 78(10): 1298-1304 (2009)), IPA/NO-aspirin and DEA/NO-aspirin showed a significant decrease in cell survival. IPA/NO-aspirin, which releases HNO with a half life of approximately 6 h, reduced the number of cells in cell culture media at a micro-molar concentration. DEA/NO-aspirin, an NO releasing aspirin, also showed cytotoxicity but has a higher $IC_{50}$ value compared to IPA/NO-aspirin.

In MCF-7 cells, the $IC_{50}$ of IPA/NO-aspirin was found to be 90 μm while that of DEA/NO-aspirin was found to be 120 μM. In MB-468 cells, the $IC_{50}$ of IPA/NO-asprin was found to be 80 μM and that of DEA/NO-aspirin was found to be 85 μM. In MB-231 cells, the $IC_{50}$ of IPA/NO-aspirin was found to be 95 μM and that of DEA/NO aspirin was found to be 90 μM. These $IC_{50}$ values were determined by MTT assay.

Example 17

This example demonstrates that nitric oxide and nitroxyl releasing (NONO)-aspirin inhibits cell proliferation of breast cancer cells.

The effect of NONO-aspirin on cell proliferation was studied using an MTT assay. The effect of DEA/NO-ASA, IPA/NO-ASA, aspirin, IPA/NO and DEA/NO was measured using the MTT assay. Cells were plated at a concentration of 8,000-10,000 cells per well in a 96 well plate and grown overnight. Cells were treated with different concentrations of the compounds and controls for 48 h. After 48 h, a solution of 5 mg/ml MTT was added to each well and incubated for 1 h. Then the media was removed from each well and 100 uL DMSO was added to each well and the absorbance was read at 550 nm. Inhibition of growth with different treatments was reported as percentage of corresponding control.

Figure 8A:
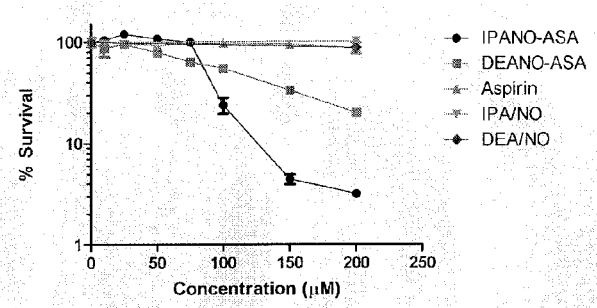
FIGS. 8A-8D are graphs showing the effect of nitric oxide and nitroxyl releasing (NONO)-aspirin and appropriate controls on cell survival of MDA-MB-231 (FIG. 8A), MDA-MB-468 (FIG. 8B), MCF-7 (FIG. 8C) and MCF-10A (FIG. 8D) cell lines. Cells were treated with various concentrations of compounds and controls as described above. Cell survival was determined using MTT after 48 h.
Figure 8B:
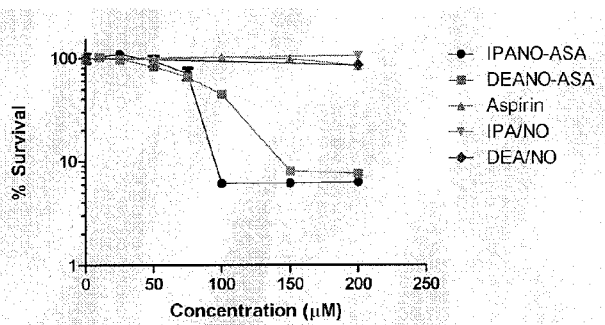
Figure 8C:
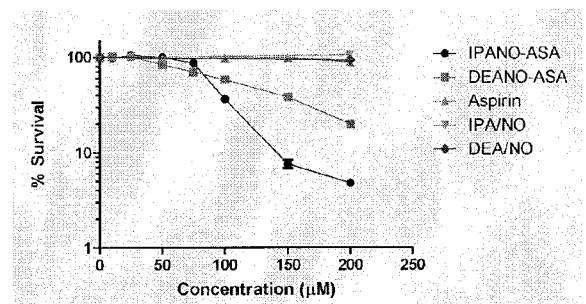
Figure 8D:
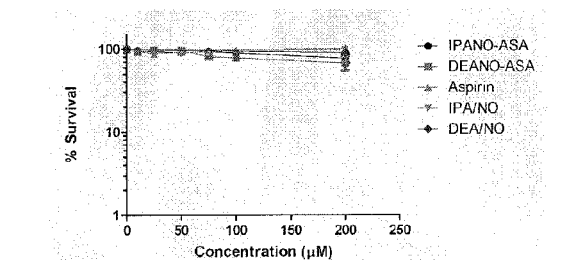

As shown in FIG. 8A (MDA-MB-231), FIG. 8B (MDA-MB-468), FIG. 8C (MCF-7), and FIG. 8D (MCF-10A), both of the compounds showed a concentration dependent decrease in cell survival after 48 h of treatment, with IPA/NO-aspirin being more potent than DEA/NO-aspirin even though the extent of cell death varies with cell line. The $IC_{50}$ value for IPA/NO-aspirin was 50 μM and the $IC_{50}$ value for DEA/NO-aspirin was 75 μM. MDA-MB-468 showed a much higher cell death with DEA/NO-aspirin due to higher susceptibility to NO. Interestingly, none of the compounds showed any significant cytotoxicity towards MCF-10A, which is a normal mammary epithelial cell line.

Example 18

This example demonstrates that NONO-aspirin induces apoptosis of cancer cells.

To evaluate the mechanism of action involved in cell death, the effect of NONO-aspirins was studied on caspase-3 activity. Caspases are cysteine proteases, which are cleaved after an aspartate residue to initiate two types of death signal transduction cascades mediated either by the binding of death ligands to a cell death receptor or mitochondria. Caspase-3 is a common mediator of both pathways of apoptosis.

The caspase-3 activity in the presence of IPA/NO-ASA and DEA/NO-ASA was measured using caspase-3 fluorescence assay kit (Cat No. 10009135, Cayman Chemical). Cells were plated at a concentration of 50,000 cells per well in a 96 well plate and grown overnight. Then the cells were treated with different concentrations of the compounds and controls for 12 h. After 12 h, the plate was centrifuged at 800 g and the media was removed by aspiration. 100 μL of lysis buffer was added to each well and the plate was incubated for min at room temperature. 100 μL of a caspase-3 substrate solution was added to each well and incubated for 30 min after which the fluorescence was read at excitation of 485 nm and emission of 535 nm.

TABLE 6

| | Caspase-3 Activity (U/mL) | |
|---|---|---|
| | IPA/NO-ASA | DEA/NO-ASA |
| MDA-MB-231 Concentration (μM) | | |
| 0 | 0.21 | 0.21 |
| 25 | 0.40 | 0.25 |
| 50 | 0.48 | 0.24 |
| 100 | 0.55 | 0.31 |
| MDA-MB-468 Concentration (μM) | | |
| 0 | 0.38 | 0.38 |
| 25 | 0.60 | 0.40 |
| 50 | 0.60 | 0.38 |
| 100 | 0.50 | 0.81 |
| MCF-7 Concentration (μM) | | |
| 0 | 0.20 | 0.20 |
| 25 | 0.30 | 0.30 |
| 50 | 0.60 | 0.35 |
| 100 | 0.58 | 0.27 |

As shown in Table 6, IPA/NO-aspirin induced a concentration dependent increase in caspase-3 activity with DEA/NO-aspirin showing no significant change as compared to control. Only in the MDA-MB-468 cell line did DEA/NO-aspirin show a significant increase which is consistent with the cell survival assay. IPA/NO-aspirin-induced caspase-mediated apoptosis after 24 h of treatment. Without wishing to be bound by any theory, one way to rationalize the insignificant change in caspase-3 activity upon treatment with DEA/NO-aspirin, in spite of cell death, is late apoptosis or necrosis due to formation of various ROS and RNS side products at a high concentration. Activity of caspase-3 can be blocked by s-nitrosylation by RNS, which can in turn be denitrosylated by Fas.

Example 19

This example demonstrates that IPA/NO-aspirin increases the level of reactive oxygen species (ROS) in cancer cells.

Reactive oxygen species (ROS) have been shown to play a key role in both apoptosis and cancer. ROS such as hydroxyl radicals (OH), superoxide anions ($O_2^-$), and hydrogen peroxide ($H_2O_2$) are constantly generated in normal cells in small amounts, which are detoxified by antioxidants present in the cell. Persistent oxidative stress can result to alteration of gene expression, mutagenesis and cell death.

To investigate the role of ROS in apoptosis, the ROS level was studied in the presence of the compounds in a time dependent manner using 2',7'-dichlorofluorescein (DCF) in all four cell lines. Cells were plated at a concentration of 30,000 cells per well and grown overnight. Cells were treated with 100 μM DCF (Sigma Aldrich) and incubated for 30 min at 37° C. The cells were then washed five times with PBS pH 7.4 and 100 μM of IPA/NO-aspirin, DEA/NO-aspirin, IPA/NO, DEA/NO and aspirin were added.

IPA/NO-aspirin treated cells showed a significant increase in ROS level, indicating a possibility of oxidative damage as a cause of apoptosis, while the ROS level of DEA/NO-aspirin-treated cells was much lower.

Example 20

This example demonstrates that IPA/NO-aspirin induces DNA damage in cancer cells.

The pathological aspect of high ROS is the ability to cause oxidative damage to DNA. To further investigate this possibility, the effect of NONO-aspirin was studied on DNA damage using a comet assay in the MDA-MB-231 cell line.

Cells were plated at a concentration of 50,000 cells per well in a 12 well plate and grown overnight. Cells were treated with 50 μM IPA/NO-aspirin and 75 μM DEA/NO-aspirin for 12 h and the assay was conducted using a comet assay kit (Cat No. 4250-050-K, Trevigen, Md.) as described in the manufacturer's instructions.

Cells treated with 50 μM IPA/NO-aspirin showed significant DNA damage after 8 h of treatment similar to $H_2O_2$-treated cells as a positive control. Cells treated with 75 μM DEA/NO-aspirin were comparable to the DMSO treated control, which showed slight ROS production that is not enough to cause DNA damage.

Example 21

This example demonstrates that IPA/NO-aspirin inhibits glyceraldehyde-3-phosphate dehydrogenase (GAPDH) activity in breast cancer.

Cells were plated at a concentration of 30,000 cells per well and grown overnight. Cells were treated with 100 μM IPA/NO-aspirin and DEA/NO-aspirin for 1, 3, and 6 h after which 200 μL of KDalert lysis buffer was added to each well. The plate was incubated at 4° C. for 20 min to lyse the cells. 10 μL of cell lysate was transferred to a clean 96 well plate and 90 μL of KDalert mastermix was added to each well and the fluorescence was measured at excitation of 540 nm and emission of 570 nm.

IPA/NO-aspirin successfully inhibited GAPDH activity in breast cancer cell lines (Table 7). But interestingly, IPA/NO-aspirin did not inhibit GAPDH activity in the MCF-10A cell line.

TABLE 7

| | GAPDH Activity (U/mL) | | |
|---|---|---|---|
| | Control | IPA/NO-ASA | DEA/NO-ASA |
| MDA-MB-231 Treatment time (h) | | | |
| 1 | 0.150 | 0.120 | 0.150 |
| 3 | 0.170 | 0.070 | 0.160 |
| 6 | 0.140 | 0.050 | 0.150 |
| MDA-MB-468 Treatment time (h) | | | |
| 1 | 0.060 | <0.010 | 0.060 |
| 3 | 0.070 | <0.010 | 0.065 |
| 6 | 0.080 | <0.010 | 0.050 |

TABLE 7-continued

| | GAPDH Activity (U/mL) | | |
|---|---|---|---|
| | Control | IPA/NO-ASA | DEA/NO-ASA |
| MCF-7 Treatment time (h) | | | |
| 1 | 0.110 | <0.010 | 0.080 |
| 3 | 0.120 | <0.010 | 0.110 |
| 6 | 0.120 | <0.010 | 0.130 |

Example 22

This example demonstrates that NONO-aspirin inhibits angiogenesis of tumor.

Angiogenesis is a key step in tumor progression by initiating recruitment of blood vessels to supply nutrients and oxygen to the growing cancer cells. NO shows a concentration effect on tumor growth. Low concentrations of NO have been shown to promote cancer cell survival, migration and proliferation and angiogenesis (Isenberg et al., *Cardiovascular Res.*, 71: 785-93 (2006)), while higher concentrations of NO have been shown to cause vascular cell growth arrest and cell death (Ridnour et al., *Antioxidants and Redox Signaling*, 8: 1329-1337 (2006)).

To determine the effect of NO and HNO releasing aspirin on angiogenesis, HUVEC cells were treated with the compounds and tube formation was studied after 12 h. Matrigel (50 μL) was added to each well in a 96 well plate and incubated for 2 h at 37° C. Cell suspension treated with different concentrations of IPA/NO-aspirin, DEA/NO-aspirin and controls was added to each well at a concentration of 20,000 cells per well. After 12 hours, tube formation was measured using a microscope.

Both IPA/NO-aspirin and DEA/NO-aspirin showed reduced angiogenesis as compared to the control even at a 1 μM concentration.

Example 23

This example demonstrates that NONO-aspirin increases phosphorylation of p53.

DNA damage that cannot be repaired by DNA repair enzymes leads to the activation of DNA damage-sensing proteins such as P53, PARP etc., which ultimately induces apoptosis. The tumor suppressor gene p53 has been found to be mutated in 50% of human cancers and in most of these mutated cases, the function of p53 is abolished (Issaeva et al., *PNAS*, 100: 13303-07 (2003)). NO can cause activation of p53 pathways by causing accumulation of p53 due to the DNA damage induced by NO (Karbowski et al. *Cell Death Differ.* 10(8):870-80 (2003); Forrester et al. *PNAS* 93: 2442-47 (1996)).

MB-231 cells were plated at a concentration on 1E6 and grown for 24 h. Then the cells were serum starved overnight followed by treatment with 50 μM and 75 μM, respectively, of IPA/NO-aspirin and DEA/NO-aspirin for 3, 6, 12 h. The cells were harvested and lysed with lysis buffer (cell signaling). Cell lysate was centrifuged at 13,000 rpm for 20 min and the supernatant was transferred to fresh tube. Protein (20 g) of protein was loaded in each lane on a 15% tris-glycine gel and electrophoresis was completed at 120V.

Both IPA/NO-aspirin and DEA/NO-aspirin showed a time dependent increase in phosphorylation of p53 with DEA/NO-aspirin showing early time point activation (1 h) as compared to IPA/NO-aspirin (10 h).

Example 24

This example demonstrates that DEA/NO-aspirin increases E-cadherin expression at both the mRNA and protein level.

E-cadherin is a prototype of calcium-mediated membrane glycoprotein known as cadherin, which are expressed in epithelial cell lines. Loss of E-cadherin-mediated cellular adhesion is a prerequisite for the invasion and metastasis of tumor cells (Birchmeier et al., *Biochimica et Biophysica Acta-Reviews on Cancer*, 1198(1): 11-26 (1994)).

MDA-MB-231 cells were plated at a concentration of 500,000 cells per plate on 60 mm plate and grown overnight. They were then treated with 100 μM of IPA/NO-aspirin, DEA/NO-aspirin, IPA/NO, DEA/NO and aspirin for 1 to 24 h.

While IPA/NO-aspirin did not show any significant change in E-cadherin level, DEA/NO-aspirin increased E-cadherin expression at both the mRNA and protein level. This can result in a reversal of tumor cells from an invasive, mesenchymal, to a benign, epithelial phenotype ((Birchmeier et al., *Biochimica et Biophysica Acta-Reviews on Cancer*, 1198(1): 11-26 (1994)).

Example 25

This example demonstrates that IPA/NO-aspirin and DEA/NO-aspirin reduce tumor size in vivo.

40 Nude mice were implanted with 7.5E5 MB-231 cells stably transfected with green fluorescent protein (GFP) per animal and allowed to grow for 14 days. The animals were randomly divided into four groups: untreated as a control, aspirin treated, IPA/NO-aspirin and DEA/NO-aspirin. Treated groups were injected daily with equi-molar dosages of the corresponding compounds (DEA/NO-aspirin=16.25 mg/Kg, IPA/NO-aspirin=15.75 mg/Kg, Aspirin=9 mg/Kg) for the next 5 weeks daily and the tumor size was measured using in vivo fluorescent imaging for quantification of the GFP tag (FIG. 9A (mammary tumor) and FIG. 9B (brain tumor)). The animals were then sacrificed to assess their brain for metastasis.

Figure 9A:
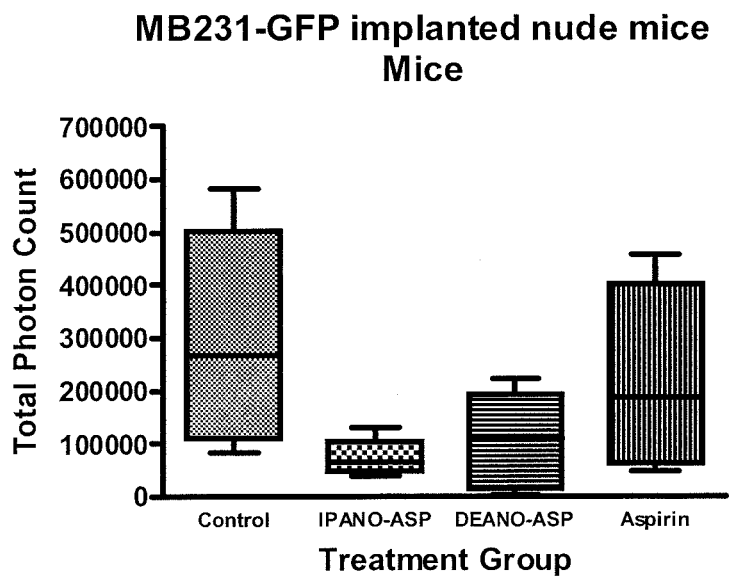
FIGS. 9A-9B are graphs showing the effect of NONO-aspirin derivatives and their controls in nude mice models implanted in with MDA-MB-231-GFP cells to form mammary tumors (FIG. 9A) or brain tumors (FIG. 9B).
Figure 9B:
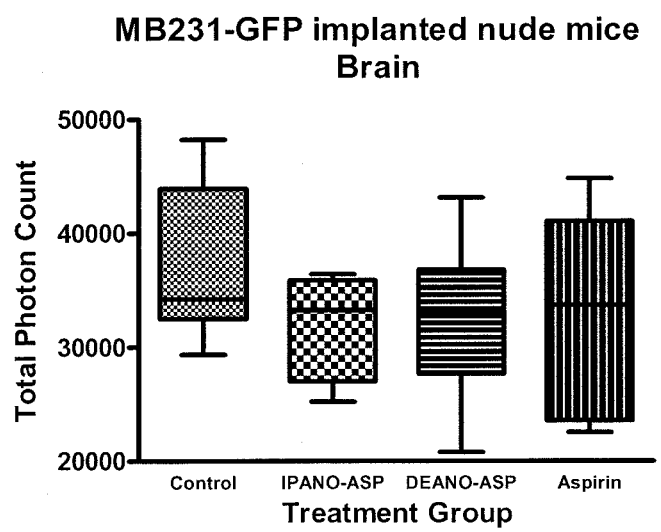

The aspirin-treated group did not show a significant decrease in tumor size as compared to the control (FIGS. 9A and 9B). However, both IPA/NO-aspirin and DEA/NO-aspirin were effective in reducing the tumor size, with IPA/NO-aspirin being more effective compared to the DEA/NO-aspirin (FIGS. 9A and 9B).

Example 26

This example demonstrates a method of synthesis of IPA/NO-indomethacin and IPA/NO-niflumic in accordance with an embodiment of the invention.

IPA/NO-indomethacin and IPA/NO-niflumic were synthesized via the following Scheme illustrated in Example 6.

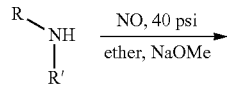

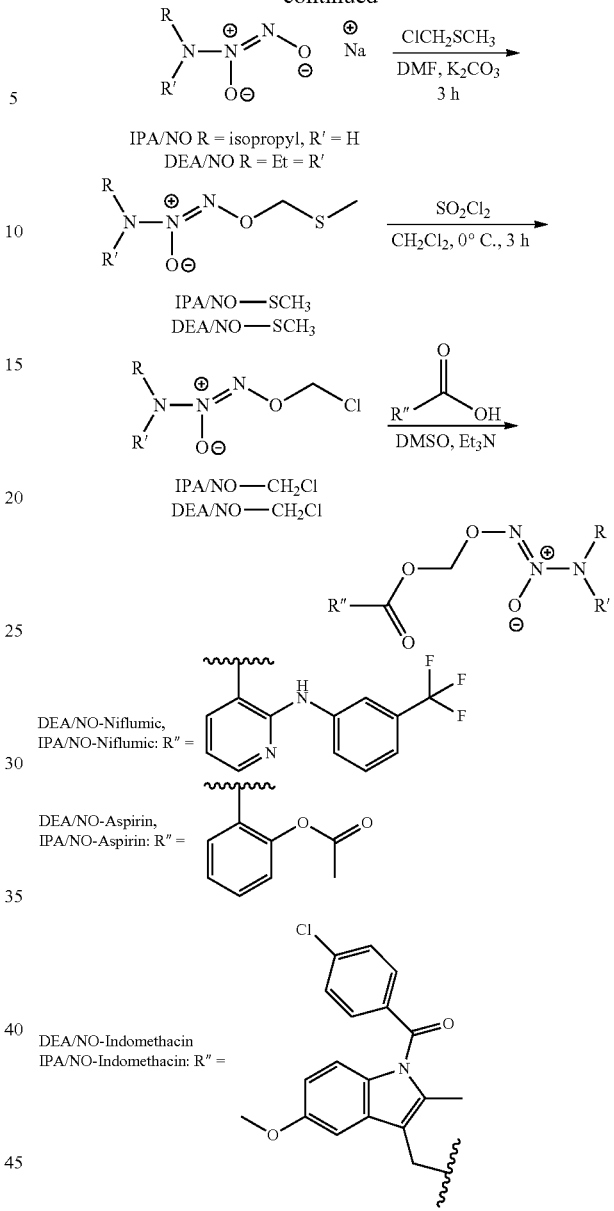

$O^2$-(2-(3-(trifluoromethyl)phenylamino)nicotinate)-1-(N,N-Diethylamino)-diazen-1-ium-1,2-diolate Niflumic acid (6.21 g, 22 mmol) was dissolved in DMSO (150 mL). Triethylamine (3.07 mL, 22 mmol) was then added and the reaction mixture was stirred for 30 min at room temperature. A solution of $O^2$-(Chloromethyl)-1-(N,N-Diethylamino)diazen-1-ium-1,2-diolate (4.0 g, 22 mmol) in DMSO (50 mL) was added drop wise to the reaction mixture. The reaction mixture was stirred for 24 hr and after completion of the reaction; it was quenched with ethyl acetate (150 mL). The organic layer was washed with saturated $NaHCO_3$ solution (5×100 mL), dried over sodium sulfate and then evaporated to obtain the crude product. Further purification was performed by gradient column chromatography (30% ethyl acetate-hexane) to obtain 6.2 g (66.2%) of pure product.
$^1$H NMR ($CDCl_3$): δ 1.07 [t, J=3.5 Hz, 6H, $(CH_3)_2$], 3.18 [q, J=3.5 Hz, 4H, $CH_2$], 6.04 (s, 2H, $OCH_2O$), 6.75 [dd, J1=5 Hz, J2=8 Hz, 1H arom] 7.25-7.41 [m, 2H arom], 7.80 [d, J=8 Hz, 1H arom], 8.07 [s, 1H arom] 8.24-8.26[dd, J1=2 Hz, J2=8 Hz, 1H, arom] 8.39-8.40 [dd, J1=4.5 Hz, J2=2 Hz, 1H, arom], 10.16 [s, 1H, NH] $^{13}$C NMR (CDCl$_3$): δ 11.45, 47.98 87.73, 106.20, 114.07, 117.32, 119.28, 123.70, 129.160, 140.01, 140.47, 153.84, 156.01, 165.8 Elemental analysis ($C_{13}H_{17}N_3O_6$): C=50.59; H=4.72; N=16.39 (theoretical), C=50.82; H=4.55; N=16.16 (experimental), MS (LCQ, ESI): 450.1 (MNa$^+$ peak).

$O^2$-(methyl2-(1-(4-chlorobenzoyl)-5-methoxy-2-methyl-1H-indol-3-yl)acetate)-1-(N,N-Diethylamino)-diazen-1-ium-1,2-diolate Indomethacin (12.4 g, 34.68 mmol) was dissolved in DMSO (150 mL). Triethylamine (4.8 mL, 34.68 mmol) was then added and the reaction mixture was stirred for 30 min at room temperature. A solution of $O^2$-(Chloromethyl)-1-(N,N-Diethylamino)diazen-1-ium-1,2-diolate (6.3 g, 34.68 mmol) in DMSO (50 ml) was added drop wise to the reaction mixture. The reaction mixture was stirred for 24 hr and after completion of the reaction; it was quenched with ethyl acetate (150 mL). The organic layer was washed with saturated NaHCO$_3$ solution (5×100 mL), dried over sodium sulfate and then evaporated to obtain the crude product. Further purification was performed by gradient column chromatography (30% ethyl acetate-hexane) to obtain 6.67 g (38.2%) of pure product. $^1$H NMR (CDCl$_3$): δ 1.04 [t, J=7 Hz, 6H, (CH$_3$)$_2$], 2.36 [s, 3H, ArCH$_3$], 3.16 [q, J=7 Hz, 4H(CH$_2$)$_2$] 3.71 [s, 2H, ArCH$_2$], 3.83 [s, 3H, OCH$_3$], 5.8 [s, 2H, OCH$_2$O], 6.67 [dd, J=9 Hz, 2.5 Hz, 1H, Indolyl ring], 6.86 [d, J=9 Hz, 1H, Indolyl], 6.92 [d, J=2.5 Hz, 1H indolyl] 7.46-7.48 [dd, J=2 Hz, 7 Hz, benzoyl], 7.64-7.66 [dd, J=2H, 7 Hz, benzoyl] $^{13}$C NMR (CDCl$_3$): δ 11.29, 13.32, 30.17, 47.85, 55.68, 87.73, 101.04, 111.58, 111.83, 114.93, 129.12, 130.38, 130.73, 131.15, 133.79, 136.10, 139.30, 156.09, 168.24, 169.17. HRMS 503.1690 (MH$^+$ peak)

$O^2$-(2-(3-(trifluoromethyl)phenylamino)nicotinate)-1-(N-isopropylamino)-diazen-1-ium-1,2-diolate Niflumic acid (3.346 g, 11.8 mmol) was dissolved in DMSO (30 mL). Triethylamine (1.66 mL, 11.8 mmol) was then added and the reaction mixture was stirred for 50 min at room temperature. A solution of $O^2$-(chloromethyl)-1-(N-isopropylamino)diazen-1-ium-1,2-diolate in DMSO (25 mL) was added drop wise to the reaction mixture. The reaction mixture was stirred for 15 h and after completion of the reaction; the mixture was quenched with ethyl acetate (80 mL). The organic layer was washed with dil. HCl (5×60 mL), dried over sodium sulfate and evaporated to obtain the crude product. Purification was performed by column chromatography, first using 22% ethyl acetate:hexane and then 1% ethyl acetate: dichloromethane to obtain IPA/NO-niflumic (1.10 g, 2.6 mmol, 37.8%) as a light yellow solid. $^1$H NMR (CDCl$_3$): δ 1.168 [d, J=6.5 Hz, 6H, (CH$_3$)$_2$], 3.985 [s, J=6.5 Hz, 1H, CH), 5.995 (s, 2H, OCH$_2$O), 6.785 [dd, J1=5 Hz, J2=8 Hz, 1H arom] 7.287-7.444 [m, 2H arom], 7.81 [d, J=8 Hz, 1H arom], 8.048 [s, 1H arom] 8.284-8.304 [dd, J1=2 Hz, J2=8 Hz, 1H, arom] 8.417-8.431 [dd, J1=5 Hz, J2=2 Hz, 1H, arom], 10.173 [s, 1H, NH]. $^{13}$C NMR (CDCl$_3$): δ 20.37, 49.24, 87.56, 106.18, 114.11, 117.34, 119.33, 123.72, 129.20, 139.98, 140.61, 153.91, 156.02, 166.98 Elemental analysis ($C_{13}H_{17}N_3O_6$): C=50.16; H=5.50; N=13.50 (theoretical), C=49.92; H=5.42; N=13.42 (experimental), MS (LCQ, ESI ionization method): 334.1 (MNa$^+$ peak), UV: ε ($\lambda_{240\,nm}$)=7.87 mM$^{-1}$ cm$^{-1}$

$O^2$-(methyl2-(1-(4-chlorobenzoyl)-5-methoxy-2-methyl-1H-indol-3-yl)acetate)-1-(N-isopropylamino)-diazen-1-ium-1,2-diolate Indomethacin (1.5385 g, 4.3 mmol) was dissolved in DMSO (15 mL). Triethylamine (0.59 mL, 4.3 mmol) was then added and the reaction mixture was stirred for 50 min at room temperature. Then a equimolar solution of $O^2$-(2-(3-(trifluoromethyl)phenylamino)nicotinate)-1-(N-isopropylamino)-diazen-1-ium-1,2-diolate in DMSO (15 ml) was added drop wise to the reaction mixture. The reaction mixture was stirred for 15 h and after completion of the reaction; it was quenched with ethyl acetate (50 mL). The organic layer was washed with dil. HCl (5×40 mL), dried over sodium sulfate and then evaporated to obtain the crude product. Purification was performed by column chromatography, first using 22% Ethyl Acetate:Hexane and then 1% ethyl acetate: dichloromethane to obtain IPA/NO-indomethacin (46 mg, 0.094 mmol, 2.18%) as a light yellow liquid. $^1$H NMR (CDCl$_3$): δ 1.130 [d, J=6.5 Hz, 6H, (CH$_3$)$_2$], 2.36 [s, 3H, ArCH$_3$], 3.718 [s, 2H, ArCH], 3.834 [s, 3H, OCH$_3$], 3.850 [sep, J=6.5 Hz, 1H, CH] 5.773 [s, 2H, OCH$_2$O], 6.114 [m, 1H, NH], 6.678 [dd, J=9 Hz, 2.5 Hz, 1H, Indolyl ring], 6.870 [d, J=9 Hz, 1H, Indolyl], 6.951 [d, J=2.5 Hz, 1H indolyl] 7.46-7.48 [dd, J=2 Hz, 7 Hz, 2H, benzoyl], 7.64-7.66 [dd, J=2 Hz, 7 Hz, 2H, benzoyl] $^{13}$C NMR (CDCl$_3$): δ 13.32, 20.30, 30.25, 49.07, 55.74, 87.40, 101.33, 111.58, 111.66, 114.91, 129.11, 130.37, 130.78, 131.16, 133.75, 136.14, 139.31, 156.00, 168.25, 169.26

Example 27

This example demonstrates the release of NO and HNO from DEA/NO-indomethacin, DEA/NO-niflumic acid, and DEA/NO-aspirin.

Figure 10A:
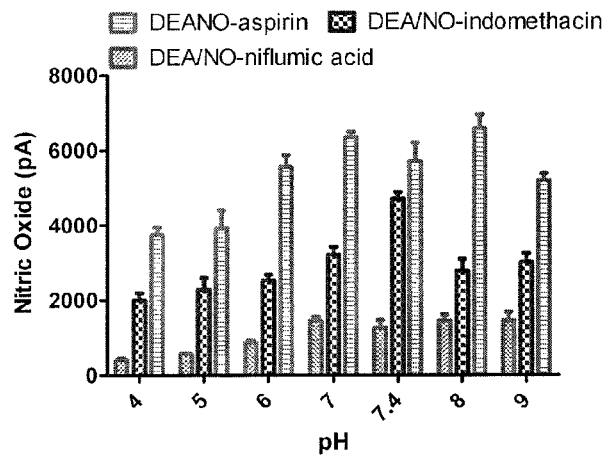
FIGS. 10A-10C are graphs showing NO release from 100 μM of DEA/NO-NSAIDs in DMSO (<0.1%) in different phosphate buffer pH 4-9 containing 2% guinea pig serum measured using NO electrode (FIG. 10A) and NO/HNO release from IPA/NO-aspirin (FIG. 10B) or IPA/NO-niflumic acid (FIG. 10C) with or without 1 mM ferricyanide.

NO release from DEA/NO-indo, DEA/NO-nifl, and DEA/NO-asp and indirect assessment of HNO release from IPA/NO-indomethacin, IPA/NO-niflumic acid, and IPA/NO-aspirin were evaluated using an NO electrode, as a function of pH (FIG. 10A).

Figure 10B:
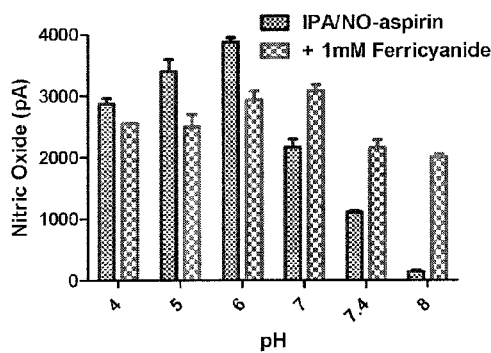
Figure 10C:
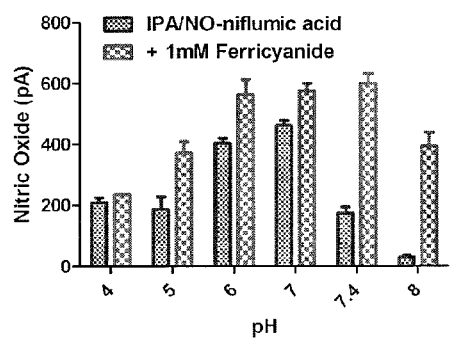

Since there is no direct method for detection of HNO, 1 mM ferricyanide solution was used as an oxidant, which converts HNO to NO, which can then be qualitatively detected using an NO electrode (FIGS. 10B-10C).

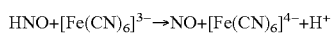

These studies were done in triplicate; in the presence of 2% Guinea pig serum. Among derivatized NSAID-NONOates, aspirin analogues were a better donors over the entire pH range due to a shorter half-life.

Example 28

This example demonstrates that DEA/NO-indomethacin, DEA/NO-aspirin, IPA/NO-niflumic acid, IPA/NO-indomethicin, and IPA/NO-aspirin penetrate cell membranes in the MB-231 cell line.

Intracellular NO/HNO release from the derivatized NSAIDs was determined using 4-amino-5-methylamino-2',7'-difluorofluoroescein diacetate (DAF-FM diacetate) as in Example 9.

The ability of the niflumic acid and indomethacin derivatized compounds to penetrate the cell membrane were tested by DAF assay in the MB-231 breast cancer cell lines. DEA/NO-indomethacin, DEA/NO-aspirin, IPA/NO-niflumic acid, IPA/NO-indomethicin, and IPA/NO-aspirin penetrated cell membranes in the MB-231 cell line.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of the formula (I) or a pharmaceutically acceptable salt thereof:

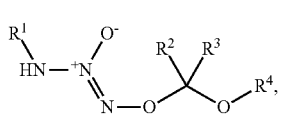

(I)

wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity, wherein the compound of the formula (I) or pharmaceutically acceptable salt thereof releases HNO at physiological pH.

2. The compound or salt of claim 1, wherein $R^1$ is optionally substituted $C_{1-12}$ alkyl, optionally substituted $C_{3-12}$ alkenyl, or optionally substituted $C_{3-8}$ cycloalkyl.

3. The compound or salt of claim 1, wherein $R^2$ and $R^3$ are the same or different and each is hydrogen, $C_{1-12}$ alkyl, aryl, or heteroaryl, each of which, other than hydrogen, is optionally substituted.

4. The compound or salt of claim 1, wherein $R^2$ and $R^3$ are hydrogen.

5. The compound or salt of claim 1, wherein $R^1$ is optionally substituted $C_{1-12}$ alkyl.

6. The compound or salt of claim 1, wherein $R^1$ is optionally substituted $C_{1-4}$ alkyl.

7. The compound or salt of claim 1, wherein $R^1$ is isopropyl.

8. The compound or salt of claim 1, wherein $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino.

9. The compound or salt of claim 8, wherein $R^5$ is an optionally substituted $C_{1-12}$ alkyl.

10. The compound or salt of claim 9, wherein the compound of formula (I) is

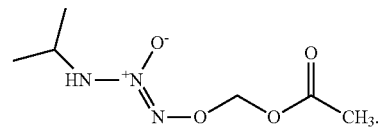

11. The compound or salt of claim 1, wherein $R^4$ is an NSAID moiety retaining its NSAID activity.

12. The compound or salt of claim 1, wherein said NSAID moiety is a moiety of an NSAID selected from the group consisting of aspirin, propionic acid derivatives, acetic acid derivatives, sulphonanilides, licofelone, enolic acid derivatives, fenamic acid derivatives, and selective COX-2 inhibitors.

13. The compound or salt of claim 1, wherein the NSAID is selected from the group consisting of aspirin, ibuprofen, naproxen, fenoprofen, ketoprofen, flurbiprofen, oxaprozin, indomethacin, sulindac, etodolac, diclofenac, piroxicam, meloxicam, tenoxicam, droxicam, lomoxicam, isoxicam, mefenamic acid, meclofenamic acid, flufenamic acid, tolfenamic acid, celecoxicab, rofecoxib, valdecoxib, parecoxib, lumiracoxib, etoricoxib, nimesulide, licofenac, and niflumic acid.

14. The compound or salt of claim 1, wherein the compound is selected from the group consisting of:

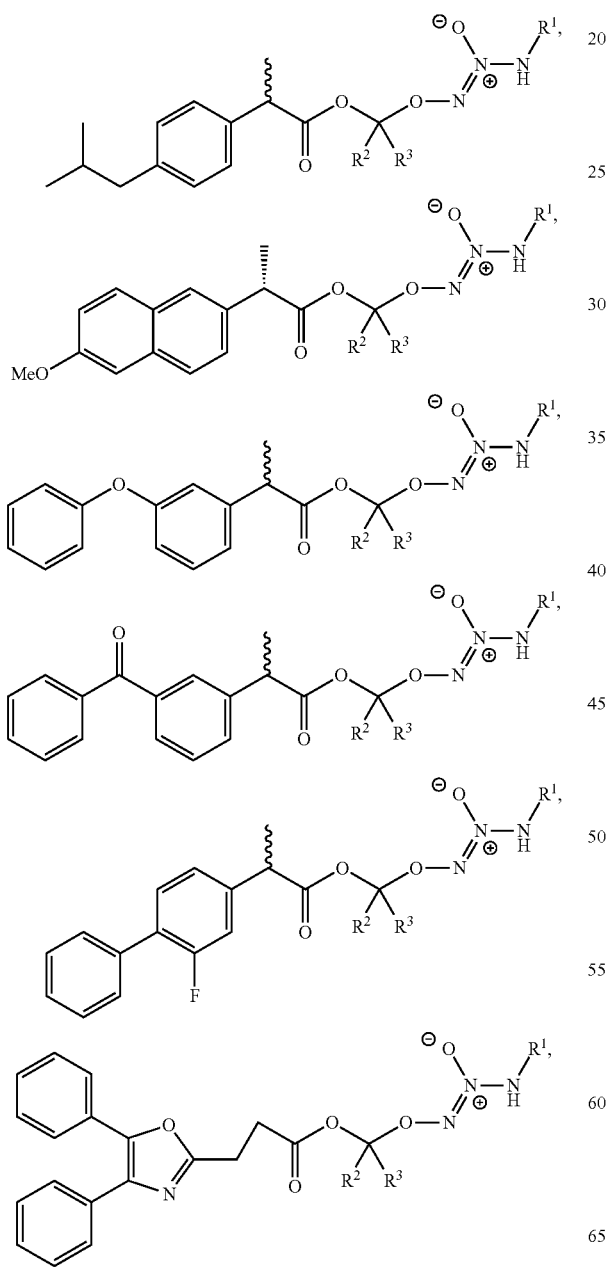

-continued

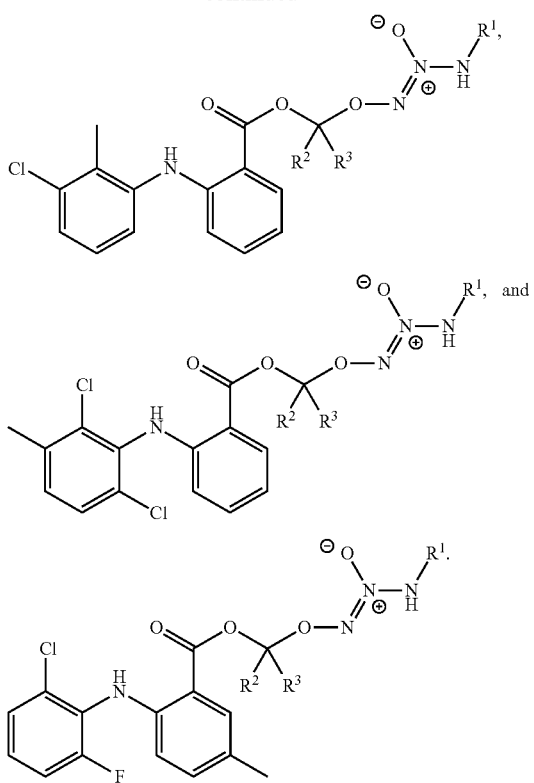

15. A compound selected from the group consisting of:

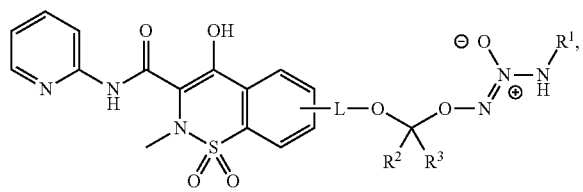

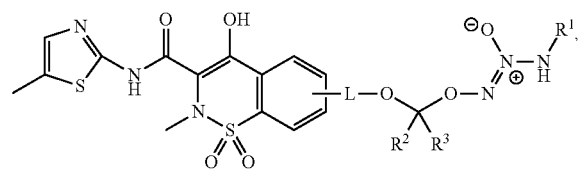

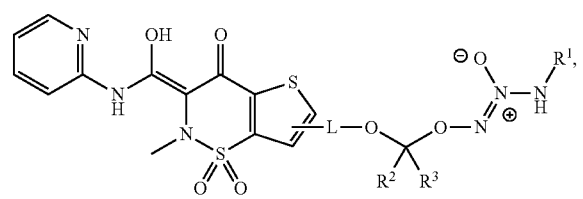

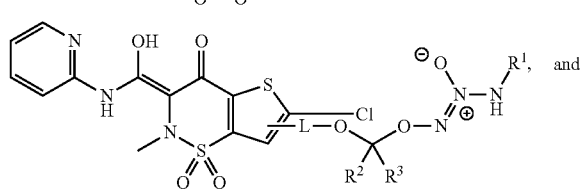

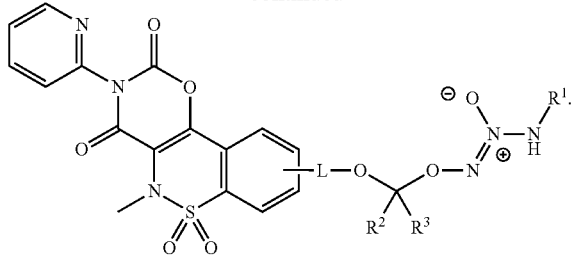

wherein:

L is a linking group selected from the group consisting of alkyl, alkenyl, alkynyl, cycloalkyl, cycloalkylalkyl, aryl, arylalkyl, carbonyl, thiocarbonyl, iminocarbonyl, carboxyl, and carbamoyl;

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocycyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or a pharmaceutically acceptable salt of the compound, wherein the compound or pharmaceutically acceptable salt releases HNO at physiological pH.

16. A compound selected from the group consisting of:

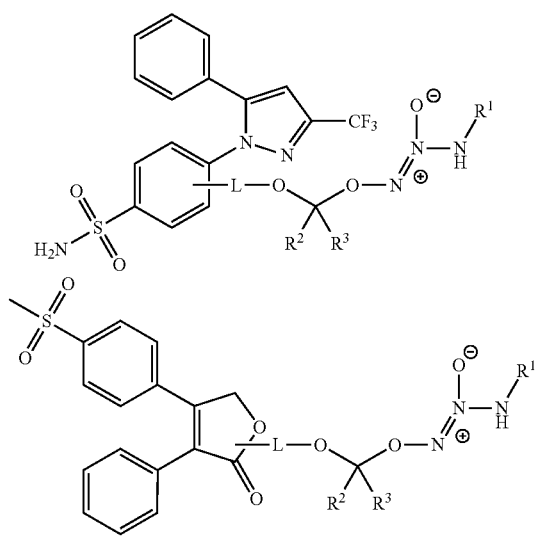

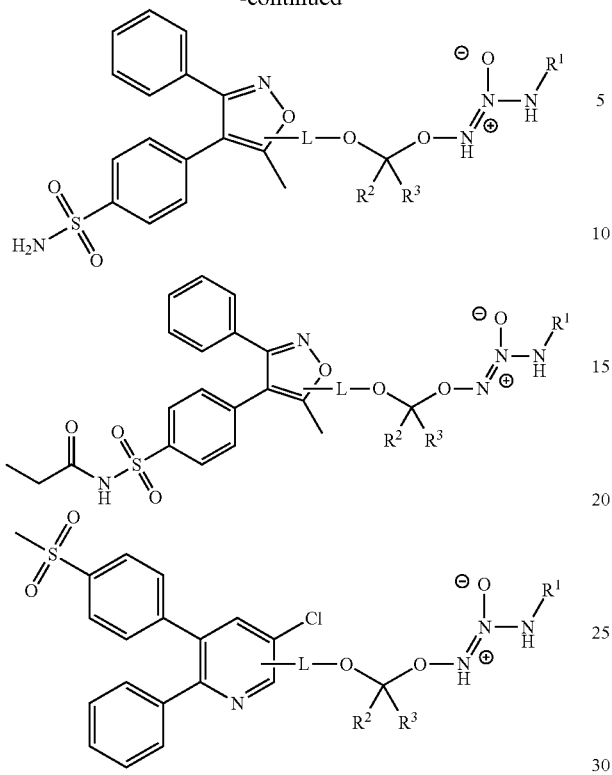

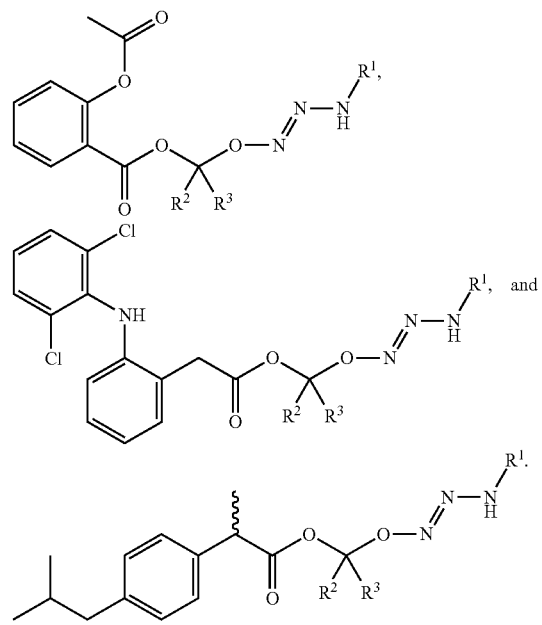

wherein:
L is a linking group selected from the group consisting of alkyl, alkenyl, alkynyl, cycloalkyl, cycloalkylalkyl, aryl, arylalkyl, carbonyl, thiocarbonyl, iminocarbonyl, carboxyl, and carbamoyl;

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^2$ and $R^3$ are the same of different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or a pharmaceutically acceptable salt of the compound, wherein the compound or pharmaceutically acceptable salt releases HNO at physiological pH.

17. The compound or salt of claim 1, wherein the NSAID is selected from the group consisting of aspirin, ibuprofen, and diclofenac.

18. The compound or salt of claim 17, wherein the compound is selected from the group consisting of:

19. The compound or salt of claim 17, wherein the NSAID is aspirin.

20. The compound or salt of claim 19, wherein the compound or salt is:

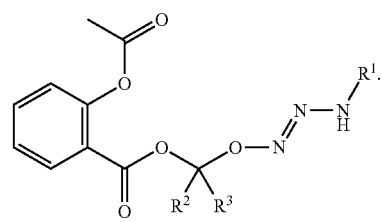

21. A pharmaceutical composition comprising (a) the compound of claim 1 or a salt thereof and (b) a pharmaceutically acceptable carrier.

22. A method of treating a disorder in an animal comprising administering an effective amount of a compound or salt of claim 1, wherein the disorder is chronic or acute heart failure, breast cancer, lung cancer, or inflammation.

23. The method of claim 22, wherein the disorder is lung cancer.

24. The method of claim 22, wherein the disorder is breast cancer.

25. The method of claim 22, wherein the compound or a salt thereof is administered under conditions where HNO is released in a greater quantity than NO.

26. The method of claim 25, wherein the compound or salt thereof releases substantially all HNO.

27. The method of claim 22, wherein the compound or salt is in a delayed release pharmaceutical composition.

28. The method of claim 22, wherein an esterase inhibiting compound is co-administered with the compound or salt thereof.

29. The method of claim 22, wherein the animal is a human.

30. The method of claim 22, wherein the disorder is chronic or acute heart failure and the compound of formula (I) is

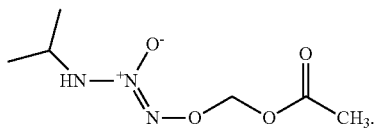
31. The method of claim 22, wherein the disorder is breast cancer or lung cancer and the compound or salt is
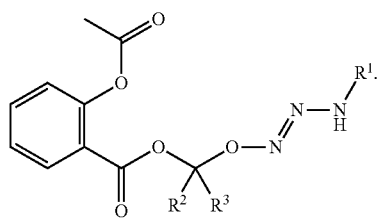
32. The method of claim 31, wherein the disorder is breast cancer.
33. The method of claim 31, wherein the disorder is lung cancer.
34. The method of claim 22, wherein the disorder is inflammation and the compound or salt is
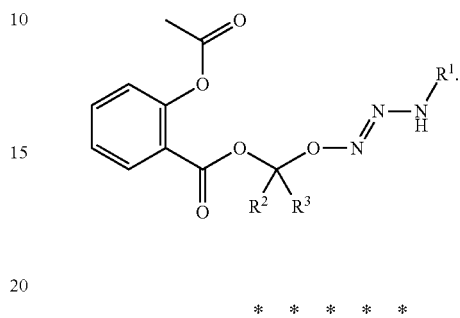
* * * * *